United States Patent [19]

Bertrandie et al.

[11] Patent Number: 5,017,569
[45] Date of Patent: May 21, 1991

[54] CEPHALOSPORIN DERIVATIVES

[75] Inventors: Alain M. Bertrandie, Cormontreuil; Thomas G. C. Bird, Witry-les-Reims; Frederic H. Jung, Rilly La Montagne; Jean-Jacques M. Lohmann, Hermonville, all of France

[73] Assignee: ICI Pharma, Gerdey Cedex, France

[21] Appl. No.: 117,619

[22] Filed: Nov. 6, 1987

[30] Foreign Application Priority Data

Nov. 12, 1986 [EP] European Pat. Off. ........ 86402515.0

[51] Int. Cl.$^5$ .................. C07D 501/38; A61K 31/545
[52] U.S. Cl. .................... 514/206; 540/221; 540/222; 540/225; 514/201
[58] Field of Search ................ 514/201, 206; 540/222, 540/225, 221

[56] References Cited

U.S. PATENT DOCUMENTS 4,279,818  7/1981  Takaya et al. ............... 424/246
4,678,781  7/1987  Jung ........................ 514/200

FOREIGN PATENT DOCUMENTS 0182210   5/1986   European Pat. Off.
0186187   7/1986   European Pat. Off.
0241901   10/1987  European Pat. Off.
0265185   4/1988   European Pat. Off.
0295630   12/1988  European Pat. Off.
1399086   6/1975   United Kingdom.
1496757   11/1978  United Kingdom.
2089339   6/1982   United Kingdom.
2148282   5/1985   United Kingdom.

Primary Examiner—Nicholas S. Rizzo
Attorney, Agent, or Firm—Cushman, Darby & Cushman

[57] ABSTRACT

Cephalosporin compounds having a 3-position substituent of the formula (I) are described:

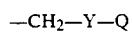

$$-CH_2-Y-Q \qquad (I)$$

wherein Y is a linking group $-NR^4CO-Y'-$, $-NR^4SO_2-Y'-$, $-OCO-Y;-$ or $-SCO-Y'-$ wherein $R^4$ is hydrogen, various optionally substituted alkyl groups or alkenyl and $Y'$ is a bond or various optionally substituted alkylene or alkenylene groups; and Q is a benzene ring (optionally fused to a further benzene ring so forming a naphthyl group or optionally fused to a 5 or 6 membered heterocyclic aromatic group containing 1, 2 or 3 heteroatoms selected from nitrogen, oxygen and sulphur), said benzene ring (or in the case of naphthyl either benzene ring) being substituted by groups $R^1$ and $R^2$ which are ortho with respect to one another, wherein $R^1$ is hydroxy or an in vivo hydrolyzable ester thereof and $R^2$ is hydroxy, an in vivo hydrolyzable ester thereof, carboxy, sulpho, hydroxymethyl, methanesulphonamido or ureido; or Q is a group of the formula (II) or (III):

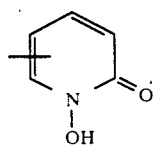

II

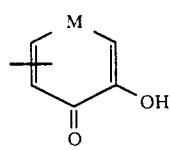

III wherein M is oxygen or a group $NR^3$
wherein $R^3$ is hydrogen or $C_{1-4}$ alkyl; ring Q being further optionally substituted.

The use of such compounds as antibacterial agents is described as are processes for their preparation and intermediates therefor.

30 Claims, No Drawings

CEPHALOSPORIN DERIVATIVES

The present invention relates to cephalosporins and in particular to such compounds comprising an amide group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans. The compounds of this invention also have non-therapeutic uses as they can be used in conventional manner in industry for example they can be used as disinfectants and food preservatives. The compounds of this invention, however, are primarily of therapeutic interest as they show a desirable profile of activity and duration in their antibacterial effect.

Investigation into new cephalosporin derivatives has been intense over the past 25 years with many thousands of patents and scientific papers having been published. A particular problem associated with the commercially available cephalosporins in the lack of potency against strains of Pseudomonas. The present invention provides cephalosporin derivatives having novel 3-position substituents, which derivatives possess good antibacterial activity and in particular against strains of Pseudomonas.

GB-B-2089339 and GB-B-2148282 disclose compounds wherein the 3-position substituent of a cephalosporin is of the formula: —CH$_2$R$^2$ wherein R$^2$ is a substituted or unsubstituted aryl, acylamino, aromatic heterocyclic, triazolyl or tetrazolyl group. U.S. Pat. No. 4,279,818 discloses compounds wherein the 3-position substituent of a cephalosporin is acyloxymethyl, hydroxymethyl, formyl or heterocyclicthiomethyl. In the above mentioned references the substituent "acyl" is able to have a variety of meanings but there is no teaching or suggestion of the compounds of the present invention which are specific ring systems characterised by having hydroxy groups or related substituents ortho to one another.

Accordingly the present invention provides a cephalosporin compound having a 3-position substituent of the formula (I):

$$-CH_2-Y-Q \quad (I)$$

wherein Q is:

(i) a benzene ring (optionally fused to a further benzene ring so forming a naphthyl group or optionally fused to a 5 or 6 membered heterocyclic aromatic group containing 1, 2 or 3 heteroatoms selected from nitrogen, oxygen and sulphur), said benzene ring (or in the case of naphthyl either benzene ring) being substituted by groups R$^1$ and R$^2$ which are ortho with respect to one another, wherein R$^1$ is hydroxy or an in vivo hydrolysable ester thereof and R$^2$ is hydroxy, an in vivo hydrolysable ester thereof, carboxy, sulpho, hydroxymethyl, methanesulphonamido or ureido;

(ii) a group of the formula (II):

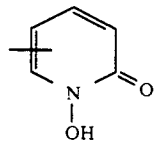

or;

(iii) a group of the formula (III):

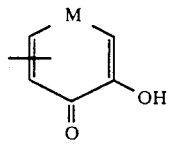

wherein M is oxygen or a group NR$^3$ wherein R$^3$ is hydrogen or C$_{1-4}$ alkyl, ring Q (or, in the case wherein ring Q is a benzene ring and is fused to another benzene ring, either benzene ring) is optionally further substituted by C$_{1-4}$ alkyl, halo, hydroxy, hydroxy C$_{1-4}$ alkyl, cyano, trifluoromethyl, nitro, amino, C$_{1-4}$ alkylamino, di-C$_{1-4}$ alkylamino, amino C$_{1-4}$ alkyl, C$_{1-4}$ alkylamino C$_{1-4}$ alkyl, di-C$_{1-4}$ alkylamino C$_{1-4}$ alkyl, C$_{1-4}$ alkanoyl, C$_{1-4}$ alkoxy, C$_{1-4}$ alkylthio, C$_{1-4}$ alkanoyloxy, carbamoyl, C$_{1-4}$ alkylcarbamoyl, di-C$_{1-4}$ alkyl carbamoyl, carboxy, carboxy C$_{1-4}$ alkyl, sulpho, sulpho C$_{1-4}$ alkyl, C$_{1-4}$ alkanesulphonamido, C$_{1-4}$ alkoxycarbonyl, C$_{1-4}$ alkanoylamino, nitroso, thioureido, amidino, ammonium, mono-, di- or tri- C$_{1-4}$ alkylammonium or pyridinium, or a 5-membered heterocyclic ring containing 1 to 4 heteroatoms selected from oxygen, nitrogen and sulphur which is optionally substituted by 1, 2 or 3 C$_{1-4}$ alkyl or C$_{1-4}$ alkoxy groups;

Y, which links into the benzene ring or the ring of formula (II) or (III), is —N(R$^4$)CO—Y$^1$—, —N(R$^4$)SO$_2$—Y$^1$—, —SCO—Y$^1$— or —OCO—Y$^1$— wherein R$^4$ is hydrogen, C$_{1-4}$ alkyl optionally substituted by any of halo, hydroxy, C$_{1-4}$ alkoxy, carboxy, amino, cyano, C$_{1-4}$ alkanoylamino, phenyl or heteroaryl, or R$^4$ is C$_{2-6}$ alkenyl; and Y$^1$ is a direct covalent bond, C$_{1-4}$ alkylene optionally substituted by any of C$_{1-4}$ alkyl, cyano, carboxy, C$_{1-4}$ alkoxycarbonyl, nitro, amino, C$_{1-4}$ alkylamino, di-C$_{1-4}$ alkylamino, C$_{1-4}$ alkanoylamino, C$_{1-4}$ alkoxy carbonylamino, hydroxy, halo, carbamoyl, C$_{1-4}$ alkylcarbamoyl, di-C$_{1-4}$ alkylcarbamoyl or trifluoromethyl, or Y$^1$ is carbonyl or C$_{2-4}$ alkenylene optionally substituted by C$_{1-4}$ alkyl.

In one aspect Y is —SCO—Y$^1$— or —OCO—Y$^1$—. In a preferred aspect Y is —N(R$^4$)CO—Y$^1$— or —N(R$^4$)SO$_2$—Y$^1$—. Suitably R$^4$ is hydrogen, methyl, ethyl, n-propyl, isopropyl, 2-fluoroethyl, 2-chloroethyl, 2-hydroxymethyl, 2-methoxyethyl, carboxymethyl, 2-aminoethyl, 2-cyanoethyl, 2-formamidoethyl, allyl, furfuryl, benzyl or pyrid-4-ylmethyl. Favourably R$^4$ is hydrogen, methyl or ethyl.

Particular values for —Y$^1$— include C$_{1-4}$ alkylene for example methylene and ethylene, C$_{1-4}$ alkylene substituted by amino for example —CH(NH$_2$)—CH$_2$—, C$_{1-4}$ alkylene substituted by C$_{1-4}$ alkanoylamino for example —CH(NHCOCH$_3$)—CH$_2$—, C$_{2-4}$ alkenylene optionally substituted by C$_{1-4}$ alkyl for example ethylene and —C(C$_2$H$_5$)=CH—.

A preferred value for —Y$^1$— is a direct covalent bond.

In a preferred aspect Y is a linking group —NH-CO—.

In another preferred aspect Y is a linking group —N(C$_2$H$_5$)CO—.

In yet another preferred aspect Y is a linking group —NHSO$_2$—.

In one aspect ring Q is benzene ring substituted by groups R$^1$ and R$^2$ as hereinbefore defined. R$^1$ is hydroxy or an in vivo hydrolysable ester thereof. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include C$_{1-6}$ alkanoyloxy for example acetoxy, propionyloxy, pivaloyloxy, C$_{1-4}$ alkoxycarbonyloxy for example ethoxycarbonyloxy, phenylacetoxy and phthalidyl.

Conveniently both R$^1$ and R$^2$ have the same value and are both hydroxy or are both in vivo hydrolysable esters, for example they are both acetoxy or both pivaloyloxy.

In one aspect Q is a ring of the formula (III). Suitably M is oxygen thus forming a pyranone ring. Suitably also M is —NH— in which case the linking group may be attached to the pyranone ring via the ring nitrogen atom or via a ring carbon atom, in the latter case allowing a greater degree of tautomerism into the hydroxypyridine tautomer. In a further aspect M is —NR$^3$ wherein R$^3$ is C$_{1-4}$ alkyl in which case the linking group Y is attached to the pyranone ring via a ring carbon atom.

In a preferred aspect Q is a benzene ring optionally fused to another benzene ring so forming a naphthyl group. As stated hereinbefore either benzene group may be substituted by R$^1$ and R$^2$ and by other optional substituents. Particular optional substituents are C$_{1-4}$ alkyl for example methyl, ethyl or isopropyl, halo for example chloro, bromo or fluoro, hydroxy, hydroxy C$_{1-4}$ alkyl for example hydroxymethyl, amino, nitro, C$_{1-4}$ alkoxy for example methoxy or ethoxy, carboxy C$_{1-4}$ alkyl for example carboxymethyl, C$_{1-4}$ alkanoylamino for example acetamido, trifluoromethyl, carboxy, carbamoyl, cyano, C$_{1-4}$ alkanesulphonamido for example methanesulphonamido, C$_{1-4}$ alkanoyl for example acetyl, C$_{1-4}$ alkanoyloxy for example acetoxy or propionoxy and C$_{1-4}$ alkoxycarbonyl for example methoxycarbonyl. Of these, favoured substituents are bromo, chloro, fluoro, nitro, cyano, hydroxy.

The skilled man will realise that when Q is a benzene ring up to 3 optional substituents are possible; when a naphthyl ring is formed more substituents are possible and up to 2 or 3 substituents are possible with the rings of formulae (II) and (III). In general, we prefer up to 2 optional substituents, which may be the same or different.

As stated herein above the present invention relates to cephalosporins having a novel 3-position substituent. A particular class of cephalosporins within the present invention is that of the formula (IV):

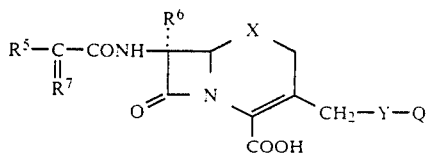

and salts and esters thereof wherein Y and Q are as hereinbefore defined;

X is sulphur, oxygen, methylene or sulphinyl;

R$^6$ is hydrogen, methoxy or formamido; and R$^5$ and R$^7$ are groups known for such positions in the cephalosporin art.

Preferably X is sulphur.

Preferably R$^6$ is hydrogen.

R$^5$ is for example 2-aminothiazol-4-yl or 2-aminooxazol-4-yl each optionally substituted in the 5-position by fluorine, chlorine or bromine, or R$^5$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R$^7$ is for example of the formula =N.O.R$^8$ (having the syn configuration about the double bond) wherein R$^8$ is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(-1-4C)alkyl, (1-4C)haloalkylcarbamoyl(1-4C)alkyl, (1-3C)haloalkyl, (2-6C)hydroxyalkyl, (1-4C)alkoxy(-2-4C)alkyl, (1-4C)alkylthio(2-4C)alkyl, (1-4C)alkanesulphinyl(1-4C)alkyl, (1-4C)alkanesulphonyl(1-4-C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or R$^8$ is of the formula V:

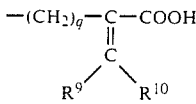

wherein q is one or two and R$^9$ and R$^{10}$ are independently hydrogen or C$_{1-4}$alkyl; or R$^8$ is of the formula VI:

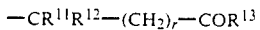

wherein r is 0-3, R$^{11}$ is hydrogen, (1-3C)alkyl or methylthio, R$^{12}$ is hydrogen (1-3C)alkyl, (3-7C)cycloalkyl, cyano, carboxy, (2-5C)carboxyalkyl or methanesulphonylamino, or R$^{11}$ and R$^{12}$ are joined to form, together with the carbon to which they are attached, a (3-7C)carbocyclic ring, and R$^{13}$ is hydroxy, amino, (1-4C)alkoxy, (1-4C) alkylamino or of the formula NHOR$^{14}$ in which R$^{14}$ is hydrogen or (1-4C)alkyl;

or R$^7$ may be of the formula =CH.R$^{15}$ wherein R$^{15}$ is hydrogen, halogen, (1-6c)alkyl, (3-7C)cycloalkyl, (2-6C)alkenyl, (3-7C)cycloalkenyl, phenyl or benzyl.

Particular meanings for R$^8$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthio-ethyl, 2-methanesulphinylethyl, 2-methanesulphonyl-ethyl, 2-aminoethyl, 3-aminopropyl, 2-methylamino ethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl and 2-oxotetrahydrofuran-3-yl.

or, when $R^8$ is of the formula V in which q is 1 or 2, a particular meaning for $R^8$ is when $R^9$ and $R^{10}$ are hydrogen or methyl.

or, when $R^8$ is of the formula VI, a particular meaning for $R^8$ is when r=0 and $R^{11}$ is hydrogen, methyl or methylthio, $R^{12}$ is hydrogen, methyl, cyclopropyl, cyclobutyl, cyclopentyl, cyclohexyl, cyano, carboxy, carboxymethyl, 2-carboxyethyl or methanesulphonylamino, or when $R^{11}$ and $R^{12}$ are joined to form, together with the carbon to which they are attached, a cyclopropane, cyclobutane, cyclopentane, cyclohexane or cycloheptane ring and $R^{13}$ is hydroxy, amino, methoxy, ethoxy, methylamino, ethylamino, or of the formula $NHOR^{14}$ in which $R^{14}$ is hydrogen, methyl or ethyl.

Preferably $R^8$ is $C_{1-6}$ alkyl for example methyl or ethyl, 1-carboxycyclobutyl, 1-carboxycyclopentyl, or 2-carboxyprop-2-yl. In particular $R^8$ is 2-carboxyprop-2-yl.

Particular meanings for $R^{15}$ are hydrogen, methyl, ethyl or chlorine.

Particular compounds of the invention include:
7-[2-(2-aminothiazol-4-yl)-2-((Z)-ethoxyimino)acetamido]-3-(3-bromo-4,5-dihydroxybenzoylaminomethyl)ceph-3-em-4-carboxylic acid, 7-[2-(2-aminothiazol-4-yl)-2-((Z)-1-carboxy-1-methylethoxyimino)acetamido]-3-(3-bromo-4,5-dihydroxybenzoylaminomethyl)ceph-3-em-4-carboxylic acid,
7-[2-(2-aminothiazol-4-yl)-2-((Z)-1-carboxy-1-methylethoxyimino)acetamido]-3-(3,4-dihydroxy-5-nitrobenzoylaminomethyl)ceph-3-em-4-carboxylic acid, 7-[2-(2-aminothiazol-4-yl)-2-((Z)-1-carboxycyclobutoxyimino)acetamido]-3-(3,4-dihydroxy-5-nitrobenzoylaminomethyl)ceph-3-em-4-carboxylic acid,
7-[2-(2-aminothiazol-4-yl)-2-((Z)-1-carboxycyclobutoxyimino)acetamido]-3-(3-cyano-4,5-dihydroxybenzoyl-aminomethyl)ceph-3-em-4-carboxylic acid,
7-[2-(2-aminothiazol-4-yl)-2-((Z)-1-carboxy-1-methylethoxyimino)acetamido]-3-(3-fluoro-4,5-dihydroxybenzoylaminomethyl)ceph-3-em-4-carboxylic acid,
7-[2-(2-aminothiazol-4-yl)-2-((Z)-1-carboxycyclopentoxyimino)acetamido]-3-(3-fluoro-4,5-dihydroxybenzoylaminomethyl)ceph-3-em-4-carboxylic acid,
7-[2-(2-aminothiazol-4-yl)-2-((Z)-1-carboxy-1-methylethoxyimino)acetamido]-3-(2,3-dihydroxy-5-fluorobenzoylaminomethyl)ceph-3-em-4-carboxylic acid, 7-[2-(2-aminothiazol-4-yl)-2-((Z)-1-carboxy-1-methylethoxyimino)acetamido]-3-((2-bromo-4,5-dihydroxyphenyl)ethenylaminomethyl)ceph-3-em-4-carboxylic acid,
7-[2-(2-aminothiazol-4-yl)-2-((Z)-1-carboxy-1-methylethoxyamino)acetamido]-3-(2,3-dihydroxy-5-bromobenzoylaminomethyl)ceph-3-em-4-carboxylic acid, 7-[2-(2-aminothiazol-4-yl)-2-((Z)-1-carboxycyclo-butoxyimino)acetamido]-3-(2,3-dihydroxy-5-bromobenzoylaminomethyl)ceph-3-em-4-carboxylic acid,
7-[2-(2-aminothiazol-4-yl)-2-((Z)-1-carboxycyclopentoxyimino)acetamido]-3-(2,3-dihydroxy-5-bromobenzoylaminomethyl)ceph-3-em-4-carboxylic acid, 7-[2-(2-aminothiazol-4-yl)-2-((Z)-1-carboxy-1-methylethoxy-imino)acetamido]-3-((1,4-dibromo-2,3-diacetoxynaphth-6-yl)carboxamidomethyl)ceph-3-em-4-carboxylic acid,
7-[2-(2-aminothiazol-4-yl)-2-((Z)-1-carboxy-1-methylethoxyimino)acetamido]-3-(2,3-dihydroxynaphth-6-yl)carboxamidomethyl)ceph-3-em-4-carboxylic acid,
7-[2-(2-aminothiazol-4-yl)-2-((Z)-1-carboxy-1-methylethoxyimino)acetamido]-3-(3,4-dihydroxy-5-isopropylbenzoylaminomethyl)ceph-3-em-4-carboxylic acid and 7-[2-(2-aminothiazol-4-yl)-2-((Z)-1-carboxycyclopentoxyimino)acetamido]-3-(3,4-dihydroxypyridinylcarboxamidomethyl)ceph-3-em-4-carboxylic acid.

The cephalosporin derivatives referred to herein are generally named in accordance with the 'cephem' nomenclature and numbering system proposed in J.A.C.S. 1962, 84, 3400.

It will be realised, of course, that the present invention covers all isomeric and tautomeric forms of the aforementioned compounds. For example the rings of the formula (III) may be in pyranone or hydroxypyridine form.

As stated hereinbefore the compounds of this invention are primarily intended for use in therapy. Therefore in a preferred aspect the present invention provides a cephalosporin compound having a 3-position substituent of the formula I or a pharmaceutically acceptable salt of ester thereof. Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, or N,N-dibenzylethylamine.

In order to use a compound of the present invention or a pharmaceutically acceptable salt or ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical compositions of this invention may be administered in standard manner for the disease condition that it is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 50% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinially used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 to 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula I, which process comprises: (a) reacting a cephalosporin compound having an optionally protected 3-position substituent of the formula: $-CH_2NHR^4$, $-CH_2OH$ or $-CH_2SH$ wherein $R^4$ is as hereinbefore defined with a compound of the formula (VII):

L—Y—Q (VII)

wherein Y and Q are as hereinbefore defined and L is a leaving group; or (b) for compounds of the formula (IV), reacting a compound of the formula (VIII) with a compound of the formula (IX) or a reactive derivative thereof:

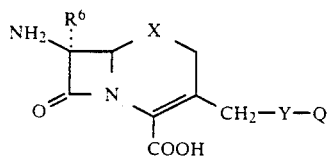

(VIII)

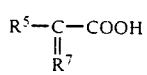

(IX)

wherein $R^5$, $R^6$, $R^7$, X, Y and Q are as hereinbefore defined; or (c) for compounds of the formula (IV) wherein $R^7$ is a group $=NOR^8$, reacting a compound of the formula (X):

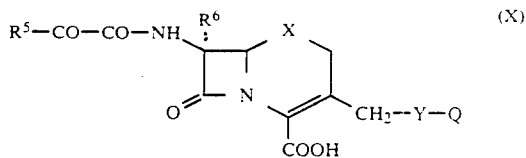

wherein $R^5$, $R^6$, X, Y and Q are as hereinbefore defined, with a compound of the formula: $R^8ONH_2$ wherein $R^8$ is as hereinbefore defined; or (d) for compounds of the formula (IV) wherein $R^7$ is a group $=NOR^8$ and $R^8$ is other than hydrogen, reacting a compound of the formula (IV) as hereinbefore defined wherein $R^7$ is a group $=NOH$ with a compound of the formula (XI):

$L^1-R^{16}$ (XI)

wherein $L^1$ is a leaving group and $R^{16}$ is a group $R^8$ other than hydrogen; or (e) for compounds of the formula (IV) forming a group $R^5$ by cyclising an appropriate precursor thereof;

wherein any functional groups are optionally protected;

and thereafter, if necessary:

(i) removing any protecting group, (ii) for preparing in vivo hydrolysable esters, esterifying corresponding hydroxy groups, (iii) converting compounds wherein X is S to compounds wherein X is sulphinyl and vice versa, (iv) forming a pharmaceutically acceptable salt.

In the reaction between a cephalosporin compound having an optionally protected 3-position substituent of the formula $-CH_2NHR^4$, $-CH_2OH$ or $-CH_2SH$ and a compound of the formula (VII), conveniently L is a leaving group such as halo for example chloro, bromo or iodo. Most suitably the reaction is performed under conditions conventional for the reaction of acid halides with amines for example in the presence of an organic amine or coupling reagents such as dicyclohexylcarbodiimide and hydroxybenztriazole. Suitably the reaction is performed at an ambient or lower temperature in a substantially inert solvent such as dimethylformamide.

The cephalosporin starting-materials for this reaction are known from the art, or are made by methods analogous to those of the art. See for example EP-A-127992 and EP-A-164944.

The compounds of the formula VII are either known in the art or are made by methods analogous thereto. For example compounds wherein L is chloro are conveniently prepared from the corresponding acids. The acids are known or are prepared by methods known to those skilled in the art, for example as in the hereinafter described Examples.

The reaction between compounds of the formulae VIII and IX is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodi-imide.

The compounds of the formula VIII can be prepared in a manner analogous to that described for the compounds of the formula I, with the 7-amino group being optionally protected.

The reaction between compounds of the formula X and R⁸ONH₂ is performed under conditions standard in the general chemical and/or cephalosporin art. The compounds of the formula X can be prepared in a manner analogous to that described for the compounds of the formula I.

The reaction between the compound of the formula IV wherein R⁷ is a group =NOH and a compound of the formula XI is performed under conditions standard in the general chemical and/or cephalosporin art.

A group R⁵ may be formed by cyclizing an appropriate precursor. For example compounds of the formulae XII and XIII,

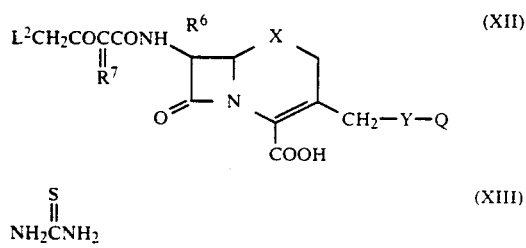

wherein R⁷, R⁶, X, Y and Q are as hereinbefore defined and L² is a leaving group, may be reacted to form a 2-aminothiazol-4-yl group. A nitrogen atom of the thiourea may be optionally protected during this cyclization.

The compounds of the formula XII can be prepared in a manner analogous to that described for the compounds of the formula I.

The compounds of the formulae IX, XI and R⁸ONH₂ are known from, or can be made by the methods of, the general chemical and/or cephalosporin art.

The compounds of the formulae VIII, X and XII are novel and as such form a further aspect of the present invention.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12C)alkyl groups, (e.g. isopropyl, t-butyl); halo lower alkyl groups (e.g. 2-iodethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl), tri(lower alkyl)silyl lower alkyl groups (e.g. trimethylsilylethyl), and (2-6C)alkenyl groups (e.g. allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (e.g. acetyl); lower alkoxycarbonyl groups (e.g. t-butoxycarbonyl; halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl) and aryl lower alkyl (e.g. benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl; di-p-anisylmethyl and furylmethyl groups; acyl (e.g. alkoxycarbonyl and aralkoxycarbonyl e.g. t-butoxycarbonyl and benzyloxycarbonyl); trialkylsilyl (e.g. trimethylsilyl and t-butyldimethylsilyl); alkylidene (e.g. methylidene); benzylidene and substituted benzylidene groups; and the phthalimido group.

The following biological test methods, data and Examples serve to illustrate this invention.

ANTIBACTERIAL ACTIVITY

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. The compounds have particularly high activity in vitro against strains of *Pseudomonas aeruginosa*.

The antibacterial properties of the compounds of the invention may also be demonstrated in vivo in conventional mouse protection tests.

In addition representative compounds of this invention show prolonged duration, as evidenced by half-life values, in test animals.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Isosensitest agar medium. The antibacterial activity is described in terms of the minimum inhibitory concentration (MIC) determined by the agar-dilution technique with an inoculum size of $10^4$ CFU/spot.

After about 2 hours the mixture was diluted with an equal volume of water.

For preparing di-acetoxy compounds the reaction mixture was poured into ice-cold water (25 ml) and the pH adjusted to 3.5 with 2 N HCl. The resultant mixture was partitioned with dichloromethane and the organic phase dried ($MgSO_4$) and evaporated to an oil which was subjected to chromatography on Dianion HP 20 SS resin eluting with water/acetonitrile (gradient elution). Concentration of the appropriate fractions followed by trituration with ether gave the product as an amorphous solid.

For preparing dihydroxy compounds directly from

| | MIC (μl/ml) EXAMPLE | | | | | | | | | | | | | | | | |
|---|---|---|---|---|---|---|---|---|---|---|---|---|---|---|---|---|---|
| ORGANISM | 4 | 11 | 15 | 17 | 35 | 44 | 47 | 67 | 76 | 78 | 79 | 84 | 97 | 90 | 85 | 110 | 118 | 126 |
| P. aeruginosa PU21 (A8101028) | 0.06 | 0.015 | 0.008 | 0.008 | 0.008 | 0.008 | 0.015 | 0.06 | 0.06 | 0.125 | 0.06 | 0.25 | 0.015 | 0.25 | 0.03 | 0.015 | 0.06 | 0.03 |
| Ent. cloacae P99 (A8401054) | 0.015 | 0.03 | 0.03 | 0.03 | 0.06 | 0.015 | 0.015 | 0.25 | 0.125 | 0.125 | 0.06 | 0.125 | 0.03 | 1 | 0.06 | 0.03 | 0.5 | 0.5 |
| Serr. marcesens (A8421003) | 0.008 | 0.008 | 0.008 | 0.008 | 0.008 | 0.008 | 0.008 | 0.06 | 0.015 | 0.03 | 0.015 | 0.03 | 0.008 | 0.125 | 0.015 | 0.008 | 0.5 | 0.015 |
| Pr. morganii (A8433001) | 0.03 | 0.03 | 0.015 | 0.03 | 0.125 | 0.03 | 0.06 | 0.125 | 0.125 | 0.125 | 0.06 | 0.06 | 0.008 | 0.5 | 0.06 | 0.015 | 0.25 | 0.125 |
| Kleb. aerogenes (A8391027) | 0.008 | 0.008 | 0.008 | 0.008 | 0.008 | 0.008 | 0.008 | 0.015 | 0.008 | 0.015 | 0.008 | 0.008 | 0.008 | 0.06 | 0.008 | 0.008 | 0.06 | 0.008 |
| E. coli DCO (A8341098) | 0.008 | 0.008 | 0.008 | 0.008 | 0.008 | 0.008 | 0.008 | 0.008 | 0.008 | 0.008 | 0.008 | 0.008 | 0.008 | 0.015 | 0.008 | 0.008 | 0.06 | 0.008 |
| St. aureus 147N (A8601052) | 4 | 16 | 16 | 16 | 16 | 16 | 8 | 16 | 16 | 32 | 32 | 32 | 16 | 64 | 16 | 32 | 128 | 8 |
| S. dublin (A8369001) | 0.015 | 0.015 | 0.008 | 0.008 | 0.008 | 0.008 | 0.008 | 0.06 | 0.015 | 0.03 | 0.015 | 0.03 | 0.015 | 0.25 | 0.015 | 0.008 | 0.25 | 0.015 |
| Strep. pyogenes (A681018) | NA | NA | 0.5 | 0.5 | 0.25 | 0.25 | 0.25 | 1 | 0.125 | 0.25 | NA | NA | 1 | | 0.125 | NA | 0.25 | 0.5 | 0.06 |

The NMR spectra are taken at 90 MHz or 200 MHz and are quoted in terms of delta values in parts per million (ppm) with reference to tetramethylsilane (delta=0). The solvent used was $DMSOd_6/CD_3COOD/TFAd$ except where otherwise indicated. In the quotation of NMR data s=singlet, d=doublet, t=triplet, q=quartet, m=multiplet, br=broad.

EXAMPLES 1–84

The following general procedure was used for the preparation of the compounds of Examples 1–84, of which particulars are given in Tables I and II.

To a suspension of the appropriate 7-substituted 3-aminomethylceph-3-em-4-carboxylic acid (0.5 mmole) is methanol (10 ml) at 0° C. was added, rapidly, triethylamine (1.0 mmole) followed by the appropriate diacetoxy-protected carbonyl chloride or derivative thereof (for example diacetoxybenzoyl chloride) (0.5 mmole).

the reaction mixture the pH was adjusted to and maintained at 8.5 to hydrolyse the acetoxy groups. The mixture was then acidified to pH 3.5 with aqueous 2 N HCl, evaporated to dryness and purified on a Diaion HP 20 SS resin column using methanol/water mixtures of increasing proportions of methanol and containing acetic acid.

Evaporation and freeze drying of the appropriate fractions gave the product in the yield indicated.

For preparing dihydroxy compounds from purified diacetoxy compounds, the di-acetoxy compound was stirred in water at pH 8.7 for 3 hours with dropwise addition of aqueous 5% ammonium hydroxide to maintain the pH. The solution was concentrated, the pH adjusted to 3.5 and the precipitate collected by filtration and triturated with acetonitrile/ether to give the dihydroxy compound in the yield indicated.

Particulars of the compounds prepared, and the yields obtained are given in Table I. NMR characterising data are given in Table II.

TABLE I
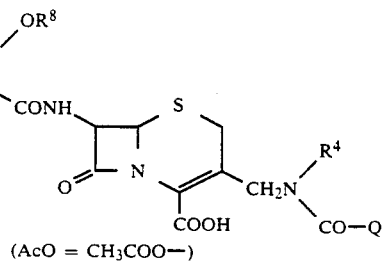
(AcO = CH₃COO—)
| Example No. | $R^8$ | $R^4$ | Q | Yield (%) | Footnotes |
|---|---|---|---|---|---|
| 1 | —CH₂CH₃ | H | 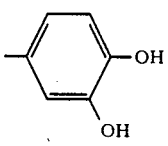 | 41 | |
| 2 | —CH₂CH₃ | H | 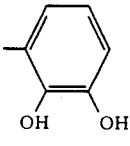 | 67 | |
| 3 | —CH₂CH₃ | H | 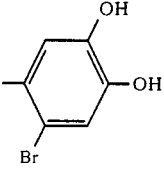 | 37 | |
| 4 | —CH₂CH₃ | H | 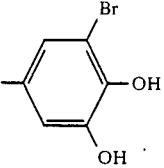 | 43 | |
| 5 | —CH₂CH₂F | H | 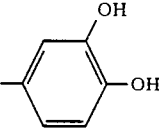 | 43 | |
| 6 | —CH₂CF₃ | H | 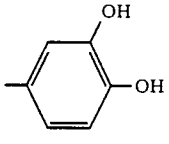 | 80 | |
| 7 | —CH₂CF₃ | H | 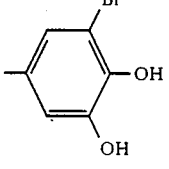 | 51 | |
| 8 | —CMe₂COOH | H | 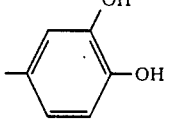 | 80 | |

TABLE I-continued
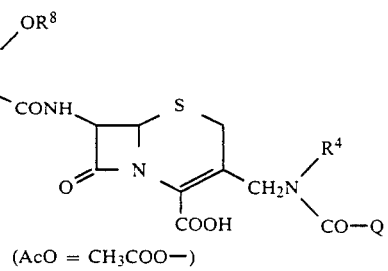
(AcO = CH₃COO—)
| Example No. | R⁸ | R⁴ | Q | Yield (%) | Footnotes |
|---|---|---|---|---|---|
| 9 | —CMe₂COOH | H | 3-methyl-catechol (2,3-dihydroxyphenyl, methyl at 1) | 37 | |
| 10 | —CMe₂COOH | H | 5-bromo-3,4-dihydroxyphenyl | 45 | |
| 11 | —CMe₂COOH | H | 3-bromo-4,5-dihydroxyphenyl | 45 | |
| 12 | —CH₂·CO₂H | H | 3,4-dihydroxyphenyl | 35 | |
| 13 | —CH₂CH₃ | —CH₂CH₃ | 5-bromo-3,4-dihydroxyphenyl | 20 | |
| 14 | —CH₂CH₃ | H | 3,4-dihydroxy-5-nitrophenyl | 21 | |
| 15 | —CMe₂COOH | H | 3,4-dihydroxy-5-nitrophenyl | 73 | |

TABLE I-continued
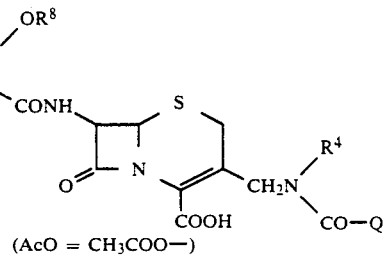
(AcO = CH₃COO—)
| Example No. | R⁸ | R⁴ | Q | Yield (%) | Footnotes |
|---|---|---|---|---|---|
| 16 | cyclobutyl-CO₂H | H | 3-Br-4,5-(OH)₂-phenyl | 16 | |
| 17 | cyclobutyl-CO₂H | H | 3-NO₂-4,5-(OH)₂-phenyl | 54 | |
| 18 | —CH₂CH₃ | H | 3-Br-4,5-(OH)₂-phenyl | 45 | |
| 19 | —CMe₂COOH | H | 3-Br-4,5-(OH)₂-phenyl | 35 | |
| 20 | —CH₂CH₃ | —CH₂CH₃ | 3-NO₂-4,5-(OH)₂-phenyl | 14 | |
| 21 | —CMe₂COOH | —CH₂CH₃ | 3-Br-4,5-(OH)₂-phenyl | 22 | |
| 22 | cyclopentyl-COOH | H | 3-Br-4,5-(OH)₂-phenyl | 22 | |
| 23 | —CMe₂COOH | H | 3,4-(OAc)₂-phenyl | 83 | 1 |

TABLE I-continued
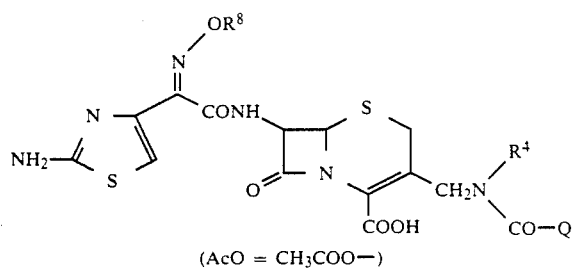
(AcO = CH₃COO—)
| Example No. | R⁸ | R⁴ | Q | Yield (%) | Footnotes |
|---|---|---|---|---|---|
| 24 | —CH₃ | H | (3,4-dihydroxyphenyl) | 54 | |
| 25 | —CMe₂COOH | —(CH₂)₂—NH₂ | (3,4-dihydroxyphenyl) | 21 | |
| 26 | —CH₃ | H | —CH₂—(3,4-diacetoxyphenyl) | 41 | 1 |
| 27 | —CH₃ | H | —CH₂—(3,4-dihydroxyphenyl) | 52 | |
| 28 | —CMe₂COOH | —(CH₂)₂—CN | (3,4-dihydroxyphenyl) | 15 | |
| 29 | 1-carboxycyclobutyl | H | (3,4-dihydroxyphenyl) | 28 | |
| 30 | 1-carboxycyclopentyl | H | (3,4-dihydroxyphenyl) | 16 | |
| 31 | —C₂H₅ | H | (2-hydroxy-3-methanesulfonamidophenyl) | 8 | |

TABLE I-continued
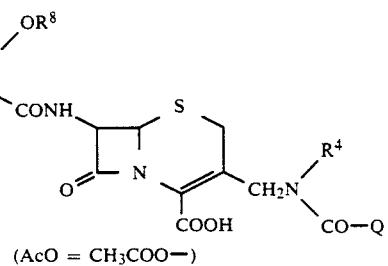
(AcO = CH₃COO—)
| Example No. | $R^8$ | $R^4$ | Q | Yield (%) | Footnotes |
|---|---|---|---|---|---|
| 32 | —CMe₂COOH | H | 3,4,5-trihydroxyphenyl | 73 | 2 |
| 33 | —CMe₂COOH | H | 3,5-dichloro-4-hydroxy... (3,5-Cl₂, 4-OH with additional OH) | 65 | 2 |
| 34 | —CMe₂COOH | H | 3-CN-4,5-(OH)₂-phenyl | 42 | 2 |
| 35 | 1-carboxycyclobutyl | H | 3-CN-4,5-(OH)₂-phenyl | 39 | 2 |
| 36 | —CH₂CH₃ | H | 3-CN-4,5-(OH)₂-phenyl | 28 | |
| 37 | —CMe₂COOH | H | 3-Br-2,4,5-(OH)₃... | 32 | 2 |
| 38 | —CMe₂COOH | —CH₂CH₃ | 3-NO₂-4,5-(OH)₂-phenyl | 36 | |

TABLE I-continued
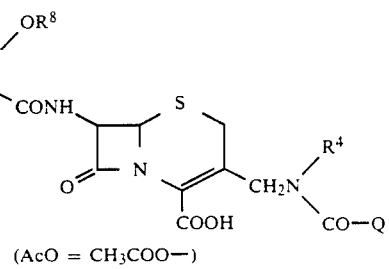
(AcO = CH₃COO—)
| Example No. | $R^8$ | $R^4$ | Q | Yield (%) | Footnotes |
|---|---|---|---|---|---|
| 39 | —CMe₂COOH | H | 3-OH, 4-OH, 5-Cl phenyl | 64 | 2 |
| 40 | —CMe₂COOH | H | 2-Cl, 3-OH, 4-OH phenyl | 84 | 2 |
| 41 | —CH₂CH₃ | H | 3-OH, 4-OH, 5-Cl phenyl | 39 | |
| 42 | —CMe₂COOH | —CH₂CH₃ | 3-OH, 4-OH, 5-CN phenyl | 20 | 2 |
| 43 | —CMe₂COOH | —CH₂CH₃ | 3-OH, 4-OH, 5-Cl phenyl | 31 | 2 |
| 44 | —CMe₂COOH | H | 3-F, 4-OH, 5-OH phenyl | 36 | 2 |
| 45 | —CMe₂COOH | —CH₂CH₃ | 3-F, 4-OH, 5-OH phenyl | 39 | 2 |

TABLE I-continued
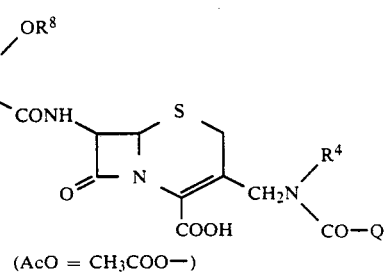
(AcO = CH₃COO—)
| Example No. | $R^8$ | $R^4$ | Q | Yield (%) | Footnotes |
|---|---|---|---|---|---|
| 46 | —CMe₂COOH | H | F-C₆H₂(OH)₂ (3,4-diOH, 5-F) | 35 | 2 |
| 47 | cyclopentyl-COOH (1-methyl) | H | F-C₆H₂(OH)₂ | 25 | 2 |
| 48 | —CMe₂COOH | —CH₂CH₃ | C₆H₂(OH)₂F₂ (diF, diOH) | 62 | 2 |
| 49 | —CH₂CH₃ | H | C₆H₂(OH)₂F | 28 | 2 |
| 50 | —CMe₂COOH | H | NO₂, (OH)₂, Cl-phenyl | 49 | 2 |
| 51 | —CH₂CH₃ | H | Cl₂(OH)₂-phenyl | 42 | |
| 52 | —CMe₂COOH | —CH₂CH₃ | F(OH)₂-phenyl | 25 | 2 |

TABLE I-continued
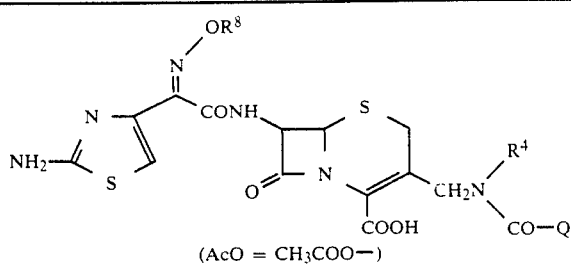
(AcO = CH₃COO—)
| Example No. | R⁸ | R⁴ | Q | Yield (%) | Footnotes |
|---|---|---|---|---|---|
| 53 | cyclopentyl-COOH | H | Cl, OH, OH, Cl (phenyl) | 55 | |
| 54 | —CH₂CH₃ | H | F, OH, OH (phenyl) | 28 | 2 |
| 55 | —CMe₂COOH | H | OH, OH, F, Br (phenyl) | 30 | 2 |
| 56 | —CMe₂COOH | H | Br, OH, OH (phenyl) | 41 | 2 |
| 57 | —CH₂CH₃ | H | Cl, OH, OH, NO₂ (phenyl) | 45 | |
| 58 | —CMe₂COOH | —CH₂CH₃ | OH, OH, F, Br (phenyl) | 36 | 2 |
| 59 | —CMe₂COOH | H | F, OH, OH (phenyl) | 75 | 2 |
| 60 | —CMe₂COOH | H | Cl, OH, OH, NO₂ (phenyl) | 42 | 2 |

TABLE I-continued
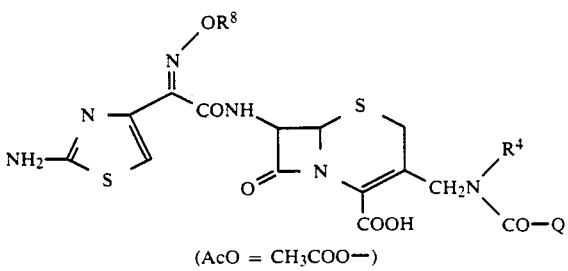
(AcO = CH₃COO—)
| Example No. | R⁸ | R⁴ | Q | Yield (%) | Footnotes |
|---|---|---|---|---|---|
| 61 | —CH₂CH₃ | H | (Br, OH, OH-substituted phenyl) | 39 | |
| 62 | —CH₂CH₃ | H | (NO₂, OH, OH, Cl-substituted phenyl) | 41 | |
| 63 | —CMe₂COOH | H | (Br, OH, OH, Br-substituted phenyl) | 58 | 2 |
| 64 | —CMe₂COOH | H | (OH, OH, Br, Br-substituted phenyl) | 33 | 2 |
| 65 | —CH₂CH₃ | H | (Br, OH, OH, Br-substituted phenyl) | 30 | |
| 66 | —CMe₂COOH | H | (Br, OH, OH, F-substituted phenyl) | 27 | 2 |
| 67 | —CMe₂COOH | H | (HO, OH, F-substituted phenyl) | 30 | 2 |

TABLE I-continued

[Structure: 2-aminothiazole with N-OR⁸ oxime, CONH linked to cephem nucleus with CH₂N(R⁴)CO-Q substituent; COOH at C-4]

(AcO = CH₃COO—)

| Example No. | R⁸ | R⁴ | Q | Yield (%) | Footnotes |
|---|---|---|---|---|---|
| 68 | —CMe₂COOH | H | —CH₂—C₆H₂(Br)(OAc)(OAc) | 20 | 3 |
| 69 | —CMe₂COOH | H | —CH=CH—C₆H₂(Br)(OAc)(OAc) | 10 | 3 |
| 70 | —CMe₂COOH | H | —CO—C₆H₃(OAc)(OAc) | 9 | 3 |
| 71 | —CMe₂COOH | H | —CH₂CH₂—C₆H₃(OAc)(OAc) | 12 | 3,4 |
| 72 | —CMe₂COOH | H | —CH₂—C₆H₂(OAc)(OAc)(COOH) | 23 | 3,5 |
| 73 | —CMe₂COOH | H | —C(C₂H₅)=CH—C₆H₂(Br)(OAc)(OAc) (with additional methyl) | 56 | 3,4 |
| 74 | —CMe₂COOH | H | —CH=CH—C₆H₂(Br)(OH)(OH) | 14 | 3 |
| 75 | —CMe₂COOH | H | —CH=CH—C₆H₂(OAc)(OAc)(Br) | 33 | 3,6 |

TABLE I-continued

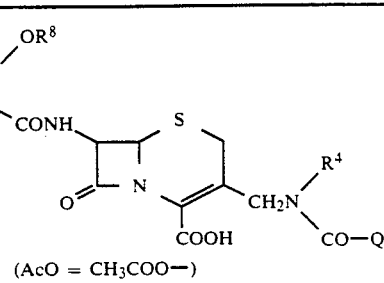

(AcO = CH₃COO—)

| Example No. | R⁸ | R⁴ | Q | Yield (%) | Footnotes |
|---|---|---|---|---|---|
| 76 | —CMe₂COOH | H | —CH=CH— (2,5-dihydroxy-4-bromophenyl, ε) | 8 | 3,7 |
| 77 | —CMe₂COOH | H | 3,4-diacetoxy-5-bromophenyl (direct attachment) | 37 | 3,7 |
| 78 | —CMe₂COOH | H | 3,4-dihydroxy-5-bromophenyl (direct attachment) | 14 | 3,6,7 |
| 79 | 1-carboxycyclobutyl | H | 3,4-dihydroxy-5-bromophenyl (direct attachment) | 7 | 3, |
| 80 | —CH₂CH₃ | H | —CH=CH— (5-bromo-3,4-diacetoxyphenyl, ε) | 31 | 3 |
| 81 | —CH₂CH₃ | H | —CH=CH— (5-bromo-3,4-dihydroxyphenyl, ε) | 30 | 3 |
| 82 | —CH₂CH₃ | H | —CH₂— (2-carboxy-4,5-diacetoxyphenyl) | 55 | 3 |

TABLE I-continued

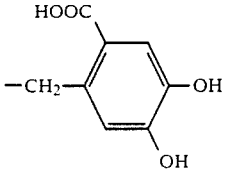

(AcO = CH₃COO—)

| Example No. | R⁸ | R⁴ | Q | Yield (%) | Footnotes |
|---|---|---|---|---|---|
| 83 | —CH₂CH₃ | H |  | 53 | 3 |
| 84 | 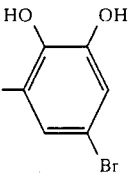 | H |  | 8 | 8 |

Footnotes
1. Deprotection to the dihydroxy compound was not performed.
2. Three equivalents of triethylamine were used.
3. The cephalsporin and triethylamine were dissolved in dimethylformamide (6 ml) to which the appropriate carbonyl chloride in dichloromethane (3 ml) was added.
4. The product was subjected to two passes through a preparative C 18 reverse phase column, firstly using methanol/water with a trace of trifluoroacetic acid (0.2%) and secondly using acetonitrile/water with trifluoroacetic acid (0.4%) as eluting solvent.
5. The corresponding anhydride was used for this reaction, prepared in situ by treatment of the di-acid with acetic anhydride. Acetic anhydride was removed by evaporation (azeotroping with toluene). One equivalent of triethylamine was used.
6. On acidifying the reaction mixture to pH 3.5 a precipitate was obtained. This was redissolved in acetonitrile (10 ml) and 0.2 M sodium acetate (50 ml) and applied directly to a Diaion HP20 SS resin column. The desired product was eluted with a water/acetonitrile gradient.
7. The product was further purified by chromatography on Diaion HP 20 SS resin using gradient elution with water/acetonitrile mixtures.
8. The trifluoroacetate salt of the cephem (0.5 mmole) in tetrahydrofuran (20 ml) was treated with bistrimethylsilylacetamide (1 mmole) for 1 hour. The appropriate acid chloride (1 equivalent) was added at 0° C. and the reaction stirred for 2 hours before diluting with ethyl acetate, washing with acid, water and brine, and evaporating to give a pale yellow solid. This was deprotected and purified in the normal manner.

TABLE II

NMR data for the compounds of Table I taken at 90 MHz in DMSOd₆/CD₃CO₂D/TFAd.

| Example No. | Delta values (ppm) |
|---|---|
| 1 | 1.25(t, 3H); 3.5(m, 2H); 4.0–4.6(m, 4H); 5.15(d, 1H); 5.75(d, 1H); 6.8(d, 1H); 7.0(s, 1H); 7.15(d, 1H); 7.3 (s, 1H). |
| 2 | 1.3(t, 3H); 3.55(m, 2H); 4.0–4.8(m, 4H); 5.15(d, 1H); 5.75(d, 1H); 7.0(s, 1H); 6.5–7.4(m, 3H). |
| 3 | 1.3(t, 3H); 3.6(m, 2H); 4.0–4.6(m, 4H); 5.15(d, 1H); 5.75(d, 1H); 6.85(s, 1H); 6.95(s, 1H); 7.0(s, 1H). |
| 4 | 1.25(t, 3H); 3.5(m, 2H); 4.0–4.6(m, 4H); 5.10(d, 1H); 5.70(d, 1H); 6.95(s, 1H); 7.3(d, 1H); 7.45(d, 1H). |
| 5 | 3.6(m, 2H); 4.2–4.7(m, 5H); 5.0(m, 1H); 5.15(d, 1H); 5.75(d, 1H); 6.8(d, 1H); 7.05(s, 1H); 7.2(d, 1H); 7.3(s, 1H). |
| 6 | 3.5(m, 2H); 4.3(q, 2H); 4.75(q, 2H); 5.15(d, 1H); 5.75(d, 1H); 6.8(d, 1H); 7.1(s, 1H); 7.2(m, 1H); 7.3(s, 1H). |
| 7 | 3.5(m, 2H); 4.3(q, 2H); 4.75(q, 2H); 5.15(d, 1H); 5.75(d, 1H); 7.1(s, 1H); 7.3(d, 1H); 7.5(d, 1H). |
| 8 | 1.53(s, 6H); 3.52(m, 2H); 4.1(d, 1H); 4.4(d, 1H); 5.14(d, 1H); 5.8(d, 1H); 6.76(d, 1H); 7.07(s, 1H); 7.2–7.4(m, 2H); |
| 9 | 1.5(s, 6H); 3.55(m, 2H); 4.35(m, 2H); 5.15(d, 1H); 5.8(d, 1H); 7.05(s, 1H); 6.5–7.4(m, 3H). |
| 10 | 1.55(s, 6H); 3.6(m, 2H); 4.25(m, 2H); 5.15(d, 1H); 5.8(d, 1H); 6.85(s, 1H); 6.95(s, 1H); 7.05(s, 1H). |
| 11 | 1.50(m, 6H); 3.5(m, 2H); 4.3(m, 2H); 5.15(d, 1H); 5.8(d, 1H); 7.0(s, 1H); 7.3(d, 1H); 7.5(d, 1H). |
| 12 | 3.5(m, 2H); 4.25(m, 2H); 4.7(s, 2H); 5.1(d, 2H); 5.75(d, 2H); 6.75(d, 1H); 7.1(s, 1H); 7.2(d, 1H); 7.3(s, 1H). |
| 13 | 1.0(t, 3H); 1.25(t, 3H); 3.1–3.6(m, 4H); 4.2(q, 2H); 4.45(s, 2H); 5.2(d, 1H); 5.75(d, 1H); 6.8(d, 1H); 7.0(d, 1H) and (s, 1H). |
| 14 | 1.25(t, 3H); 3.4–3.8(m, 2H); 4.0–4.6(m, 4H); 5.1(d, 1H); 5.75(d, 1H); 7.0(s, 1H). |
| 15 | 1.55(s, 6H); 3.55(dd, 2H); 4.35(dd, 2H); 5.15(d, 1H); 5.8(d, 1H); 7.1(s, 1H); 7.6(d, 1H); 8.0(d, 1H). |
| 16 | 1.85(m, 2H); 2.5(m, 4H); 3.5(m, 2H); 4.3(q, 2H); 5.2(d, 1H); 5.8(d, 1H); 7.05(s, 1H); 7.3(s, 1H); 7.55(s, 1H). |
| 17 | 1.85(m, 2H); 2.5(m, 4H); 3.55(dd, 2H); 4.35(dd, 2H); 5.2(d, 1H); 5.85(d, 1H); 7.1(s, 1H); 7.6(d, 1H); 8.0(d, 1H). |
| 18 | 1.2(t, 3H); 3.55(dd, 2H); 4.0–4.75(m, 4H); 5.15(d, 1H); 5.75(d, 1H); 7.0(d, 1H); 7.05(s, 1H); 7.3(d, 1H). |
| 19 | 1.55(s, 6H); 3.55(dd, 2H); 4.4(dd, 2H); 5.15(d, 1H); 5.8(d, 1H); 7.0(d, 1H); 7.05(s, 1H); 7.3(d, 1H). |
| 20 | 1.1(t, 3H); 1.3(t, 3H); 3.0–3.8(m, 4H); 4.0–4.6(m, 2H); 4.25(q, 2H); 5.15(s, 1H); 5.8(s, 1H); 7.0(s, 1H); 7.1(s, 1H); 7.4(d, 1H). |
| 21 | 1.05(t, 3H); 1.55(s, 6H); 3.0–3.8(m, 4H); 4.45(s, 2H); 5.2(d, 1H); 5.8(d, 1H); 6.85(d, 1H); 7.0(d, 1H); 7.1(s, 1H). |
| 22 | 1.7(m, 4H); 2.2(m, 4H); 3.5(m, 2H); 3.9–4.7(m, 2H); 5.15(d, 1H); 5.8(d, 1H); 7.05(s, 1H); 7.3(s, 1H); 7.5(s, 1H). |
| 23 | 1.55(m, 6H); 2.23(s, 6H); 3.4(d, 1H); 3.7(d, 1H); 4.16(d, 1H); 4.5(d, 1H); 5.16(d, 1H); 5.77(d, 1H); |

TABLE II-continued

NMR data for the compounds of Table I taken at 90 MHz in DMSOd$_6$/CD$_3$CO$_2$D/TFAd.

| Example No. | Delta values (ppm) |
|---|---|
| | 7.07(s, 1H); 7.33(d, 1H); 7.7-7.9(m, 2H). |
| 24 | 3.53(m, 2H); 3.97(s, 3H); 4.1-4.5(m, 2H); 5.17(d, 1H); 5.72(d, 1H); 6.77(d, 1H); 7.1(s, 1H); 7.15-7.4(m, 2H). |
| 25 | 1.55(s, 6H); 2.9-3.8(m, 6H); 4.5(m, 2H); 5.14(d, 1H); 5.8(d, 1H); 6.78(s, 2H); 6.9(s, 1H); 7.05(s, 1H). |
| 26 | 2.22(s, 6H); 3.36 and 3.64(2d, 2H); 3.49(s, 2H); 3.98(s, 3H); 3.98 and 4.32(2d, 2H); 5.11(d, 1H); 5.74(d, 1H); 7.0(s, 1H); 7.14(s, 3H). |
| 27 | 3.27 and 3.56(2d, 2H); 3.27(s, 2H); 3.98(s, 3H); 3.98 and 4.32(2d, 2H); 5.11(d, 1H); 5.74(d, 1H); 6.4-6.8(m, 3H); 7.0(s, 1H). |
| 28 | 1.55(s, 6H); 2.6-2.9(m, 2H); 3.2-3.8(m, 4H); 4.5(m, 2H); 5.2(d, 1H); 5.9(d, 1H); 6.78(s, 1H); 6.82(d, 2H); 7.03(s, 1H). |
| 29 | 1.95(m, 2H); 2.2(m, 4H); 3.53(br.s, 2H); 4.2(d, 1H); 4.4(d, 1H); 5.17(d, 1H); 5.88(d, 1H); 6.78(d, 1H); 7.08(s, 1H); 7.23(d, 1H); 7.28(s, 1H) |
| 30 | 1.7(m, 4H); 2.15(m, 4H); 3.53(br.s, 2H); 4.15(d, 1H); 4.4(d, 1H); 5.8(d, 1H); 5.82(d, 1H); 6.78(d, 1H); 7.05(s, 1H); 7.23(d, 1H); 7.28(s, 1H). |
| 31 | 1.28(t, 3H); 2.95(s, 3H); 3.54(br.s, 2H); 4.18(d, 1H); 4.24(q, 2H); 4.43(d, 1H); 5.16(d, 1H); 5.75(d, 1H); 6.95(d, 1H); 7.01(s, 1H); 7.57(dd, 1H); 7.77(d, 1H). |
| 32 | 1.55(s, 6H); 3.6(m, 2H); 4.3(q, 2H); 5.2(d, 1H); 5.8(d, 1H); 6.85(s, 1H); 7.05(s, 1H). |
| 33 | 1.55(s, 6H); 3.6(m, 2H); 4.3(q, 2H); 5.2(d, 1H); 5.85(d, 1H); 7.0(s, 1H); 7.05(s, 1H). |
| 34 | 1.55(s, 6H); 3.5(m, 2H); 4.3(q, 2H); 5.15(d, 1H); 5.8(d, 1H); 7.05(s, 1H); 7.55(m, 2H). |
| 35 | 1.85(m, 2H); 2.5(m, 4H); 3.5(m, 2H); 4.3(q, 2H); 5.15(d, 1H); 5.85(d, 1H); 7.05(s, 1H); 7.55(m, 2H). |
| 36 | 1.25(t, 3H); 3.5(m, 2H); 4.2(m, 4H); 5.2(d, 1H); 5.7(d, 1H); 7.0(s, 1H); 7.55(m, 2H). |
| 37 | 1.55(s, 6H); 3.6(m, 2H); 4.3(q, 2H); 5.2(d, 1H); 5.8(d, 1H); 6.45(s, 1H); 7.1(s, 1H). |
| 38 | 1.05(t, 3H); 1.55(s, 6H); 3.0-3.3(m, 4H); 4.45(m, 2H); 5.2(d, 1H); 5.85(d, 1H); 7.05(s, 1H); 7.1(s, 1H); 7.4(s, 1H). |
| 39 | 1.55(s, 6H); 3.5(m, 2H); 4.3(q, 2H); 5.15(d, 1H); 5.8(d, 1H); 7.1(s, 1H); 7.3(d, 1H); 7.4(d, 1H). |
| 40 | 1.5(s, 6H); 3.5(m, 2H); 4.2(q, 2H); 5.15(d, 1H); 5.8(d, 1H); 6.75(s, 2H); 7.05(s, 1H). |
| 41 | 1.25(t, 3H); 3.25-3.75(m, 2H); 4.0-4.6(m, 4H); 5.15(d, 1H); 5.75(d, 1H); 7.0(s, 1H); 7.3(d, 1H); 7.35(d, 1H). |
| 42 | 1.0(t, 3H); 1.55(s, 6H); 3.0-3.8(m, 4H); 4.45(m, 2H); 5.2(d, 1H); 5.85(d, 1H); 7.05(m, 3H). |
| 43 | 1.05(t, 3H); 1.55(s, 6H); 3.1-3.6; (m, 4H); 4.4(m, 2H); 5.2(d, 1H); 5.8(d, 1H); 6.8(d, 1H); 6.85(d, 1H); 7.05(s, 1H). |
| 44 | 1.55(s, 6H); 3.55(m, 2H); 4.3(q, 2H); 5.15(d, 1H); 5.8(d, 1H); 7.05-7.15(m, 3H). |
| 45 | 1.05(t, 3H); 1.55(s, 6H); 3.0-3.6(m, 4H); 4.5(m, 2H); 5.2(d, 1H); 5.85(d, 1H); 6.65(m, 2H); 7.1(s, 1H). |
| 46 | 1.55(s, 6H); 3.6(m, 2H); 4.3(q, 2H); 5.2(d, 1H); 5.8(d, 1H); 6.6(d, 1H); 7.05(s, 1H); 7.2(s, 1H). |
| 47 | 1.6-2.0(m, 4H); 2.0-2.4(m, 4H); 3.5(m, 2H); 4.3(q, 2H); 5.15(d, 1H); 5.8(s, 1H); 7.0-7.2(m, 3H). |
| 48 | 1.0(t, 3H); 1.55(s, 6H); 3.0-3.6(m, 4H); 4.5(m, 2H); 5.2(d, 1H); 5.8(d, 1H); 6.6(d, 1H); 6.7(d, 1H); 7.05(s, 1H). |
| 49 | 1.3(t, 3H); 3.5(m, 2H); 4.0-4.4(m, 4H); 5.15(d, 1H); 5.7(d, 1H); 7.0-7.2(m, 3H). |
| 50 | 1.55(s, 6H); 3.5(m, 2H); 4.3(q, 2H); 5.15(d, 1H); 5.8(d, 1H); 7.1(s, 1H); 7.25(s, 1H). |
| 51 | 1.3(t, 3H); 3.55(m, 2H); 4.0-4.45(m, 4H); 5.15(d, 1H); 5.75(d, 1H); 6.95(s, 1H); 7.0(s, 1H). |
| 52 | 1.0(t, 3H); 1.55(s, 6H); 3.0-3.8(m, 4H); 4.2-4.8(m, 2H); 5.2(d, 1H); 5.8(d, 1H); 6.65(m, 2H); 7.05(s, 1H). |
| 53 | 1.5-2.0(m, 4H); 2.0-2.4(m, 4H); 3.6(m, 2H); 4.3(q, 2H); 5.2(d, 1H); 5.8(d, 1H); 6.95(s, 1H); 7.05(s, 1H). |
| 54 | 1.25(t, 3H); 3.6(m, 2H); 4.0-4.7(m, 4H); 5.15(d, 1H); 5.8(d, 1H); 6.65(d, 1H); 7.1(s, 1H); 7.15(d, 1H). |
| 55 | 1.55(s, 6H); 3.55(m, 2H); 4.2(q, 2H); 5.15(d, 1H); 5.8(d, 1H); 7.05(s, 1H); 7.15(d, 1H). |
| 56 | 1.55(s, 6H); 3.55(m, 2H); 4.25(q, 2H); 5.15(d, 1H); 5.8(d, 1H); 6.75(s, 1H); 7.05(s, 1H). |
| 57 | 1.3(t, 3H); 3.55(m, 2H); 3.95-4.6(m, 4H); 5.15(d, 1H); 5.75(d, 1H); 7.0(s, 1H); 7.55(s, 1H). |
| 58 | 1.0(t, 3H); 1.55(s, 6H); 3.0-3.65(m, 4H); 4.55(m, 2H); 5.25(d, 1H); 5.85(d, 1H); 6.75(d, 1H); 7.05(s, 1H). |
| 59 | 1.55(s, 6H); 3.6(m, 2H); 4.2(q, 2H); 5.15(d, 1H); 5.8(d, 1H); 6.65(d, 1H); 7.05(d, 1H); 7.05(t, 1H). |
| 60 | 1.55(s, 6H); 3.6(m, 2H); 4.25(q, 2H); 5.15(d, 1H); 5.8(d, 1H); 7.05(s, 1H); 7.55(s, 1H). |
| 61 | 1.3(t, 3H); 3.6(m, 2H); 3.95-4.6(m, 4H); 5.15(d, 1H); 5.75(d, 1H); 6.75(s, 2H); 7.0(d, 1H). |
| 62 | 1.25(t, 3H); 3.5(m, 2H); 3.9-4.6(m, 4H); 5.15(d, 1H); 5.75(d, 1H); 7.0(s, 1H); 7.25(s, 1H). |
| 63 | 1.55(s, 6H); 3.6(m, 2H); 4.3(q, 2H); 5.15(d, 1H); 5.8(d, 1H); 7.05(s, 1H); 7.1(s, 1H). |
| 64 | 1.55(s, 6H); 3.65(m, 2H); 4.3(q, 2H); 5.2(d, 1H); 5.85(d, 1H); 6.85(s, 1H); 7.1(s, 1H). |
| 65 | 1.3(t, 3H); 3.6(m, 2H); 3.9-4.6(m, 4H); 5.15(d, 1H); 5.75(d, 1H); 7.0(s, 1H); 7.05(s, 1H). |
| 66 | 1.55(s, 6H); 3.65(m, 2H); 4.3(q, 2H); 5.2(d, 1H); 5.8(d, 1H); 6.8(d, 1H); 7.1(s, 1H). |
| 67 | 1.55(s, 6H); 3.55(m, 2H); 4.35(q, 2H); 5.15(d, 1H); 5.8(d, 1H); 6.75(dd, 1H); 7.1(s, 1H); 7.2(dd, 1H). |
| 68 | 1.48(d, 6H); 2.22(s, 6H); 3.38(d, 1H); 3.58(d, 1H); 3.63(s, 2H); 3.95(d, 1H); 4.26(d, 1H); 5.12(d, 1H); 5.81(d, 1H); 6.83(s, 1H); 7.24(s, 1H); 7.52(s, 1H). |
| 69 | 1.46(brs, 6H); 2.28(s, 6H); 3.43(d, 1H); 3.61(d, 1H); 4.04(d, 1H); 4.47(d, 1H); 5.15(d, 1H); 5.86(d, 1H); 6.70(d, 1H); 6.79(s, 1H); 7.60(s, 1H); 7.65(d, 1H); 7.70(s, 1H). |
| 70 | 1.45(brs, 6H); 2.28(s, 6H); 3.43(d, 1H); 3.63(d, 1H); 4.14(d, 1H); 4.48(d, 1H); 5.10(d, 1H); 5.80(d, 1H); 6.72(d, 1H); 7.33(d, 1H); 7.70-7.85(m, 2H). |
| 71 | 1.48(d, 6H); 2.26(d, 6H); 2.48(t, 2H); 2.82(t, 2H); 3.38(d, 1H); 3.44(d, 1H); 3.93(d, 1H); 4.34(d, 1H); 5.08(d, 1H); 5.82(d, 1H); 6.76(d, 1H); 7.05-7.15(m, 1H). |
| 72 | 1.48(d, 6H); 2.25(s, 6H); 3.38(d, 1H); 3.58(d, 1H); 3.90(brs, 2H); 3.92(d, 1H); 4.26(d, 1H); 5.12(d, 1H); 5.83(d, 1H); 6.78(d, 1H); 7.22(s, 1H); 7.74(s, 1H). |
| 73 | 1.48(d, 6H); 2.28(s, 6H); 3.43(d, 1H); 3.57(d, 1H); 4.08(d, 1H); 4.40(d, 1H); 5.14(d, 1H); 5.81(d, 1H); 6.80(s, 1H); 6.98(s, 1H); 7.22(s, 1H); 7.67(s, 1H). |
| 74 | 1.46(d, 6H); 3.40(d, 1H); 3.58(d, 1H); 4.04(d, 1H); 4.32(d, 1H); 5.12(d, 1H); 5.82(d, 1H); 6.45(d, 1H); 6.73(d, 1H); 6.97(d, 1H); 7.13(d, 1H); 7.25(d, 1H). |
| 75 | 1.46(d, 6H); 2.22(s, 3H); 2.32(S, 1H); 3.40(d, 1H); 3.58(d, 1H); 4.03(d, 1H); 4.34(d, 1H); 5.11(d, 1H); 5.82(d, 1H); 6.74(d, 1H); 6.78(d, 1H); 7.30(d, 1H); 7.52(d, 1H); 7.72(d, 1H). |
| 76 | 1.44(d, 6H); 3.40(d, 1H); 3.58(d, 1H); 4.02(d, 1H); 4.32(d, 1H); 5.12(d, 1H); 5.82(d, 1H); 6.70(d, 1H); 6.73(s, 1H); 6.92(d, 1H); 7.05(d, 1H); 7.62(s, 1H). |
| 77 | 1.48(d, 6H); 2.21(s, 3H); 2.26(s, 3H); 3.43(d, 1H); 3.65(d, 1H); 4.05(d, 1H); 4.42(d, 1H); 5.14(d, 1H); 5.83(d, 1H); 6.85(s, 1H); 7.67(s, 2H). |
| 78 | 1.44(brs, 6H); 3.3-3.7(m, 2H); 4.10(d, 1H); 4.55(d, 1H); 5.10(d, 1H); 5.83(d, 1H); 6.78(s, 1H); 7.02(d, 1H); 7.46(d, 1H). |
| 79 | 1.85(m, 2H); 2.5(m, 4H); 3.55(d, 1H); 3.64(d, 1H); 4.30(d, 1H); 4.56(d, 1H); 5.14(d, 1H); 5.83(d, 1H); 6.75(s, 1H); 7.03(d, 1H); 7.48(d, 1H). |
| 80 | 1.22(t, 3H); 2.27(d, 6H); 3.42(d, 1H); 3.60(d, 1H); 4.02(d, 1H); 4.08(q, 2H); 4.36(d, 1H); 5.12(d, 1H); 5.76(d, 1H); 6.70(d, 1H); 6.73(s, 1H); 7.60(s, 1H); 7.65(d, 1H); 7.69(s, 1H). |
| 81 | 1.21(t, 3H); 3.40(d, 1H); 4.04(d, 1H); 4.08(q, 2H); 4.32(d, 1H); 5.08(d, 1H); 5.76(d, 1H); 6.43(d, 1H); 6.73(d, 1H); 7.0(d, 1H); 7.08(s, 1H); 7.58(d, 1H). |
| 82 | 1.20(t, 3H); 2.24(d, 6H); 3.36(d, 1H); 3.55(d, 1H); 3.88(brs, 2H); 3.92(d, 1H); 4.11(q, 2H); 4.73(d, 1H); 5.05(d, 1H); 5.74(d, 1H); 6.74(d, 1H); 7.20(s, 1H); 7.72(s, 1H). |
| 83 | 1.23(t, 3H); 3.34(d, 1H); 3.52(d, 1H); 3.88(d, 1H); |

TABLE II-continued

NMR data for the compounds of Table I taken at 90 MHz in DMSOd$_6$/CD$_3$CO$_2$D/TFAd.

| Example No. | Delta values (ppm) |
|---|---|
|  | 4.14(q, 2H); 4.18(d, 1H); 5.05(d, 1H); 5.73(d, 1H); 6.65(s, 1H); 6.82(s, 1H); 7.33(s, 1H). |
| 84 | 1.7(m, 4H); 2.1(m, 4H); 3.42(d, 1H); 3.62(d, 1H); 4.04(d, 1H); 4.53(d, 1H); 5.10(d, 1H); 5.79(d, 1H); 6.73(s, 1H); 7.02(d, 1H); 7.50(d, 1H). |

EXAMPLES 85-99

The following general procedure was used for the preparation of the compounds of Examples 85-99 of which particulars are given in Tables III and IV.

To a suspension of the appropriate 7-substituted 3-aminomethylceph-3-em-4-carboxylic acid (0.5 mmole) in acetone (5 ml) and water (1 ml) at room temperature was added triethylamine (1.0 mmole) followed by the appropriate diacetoxybenzene or naphthalene sulphonyl chloride or derivative thereof (0.5 mmole). After about 15 minutes the organic solvent was evaporated, water (20 ml) was added to the residue and the pH adjusted and maintained at 8.0-8.5 with an aqueous solution of 5% NaHCO$_3$ to cleave the acetoxy groups.

After 3.5 hours the reaction mixture was partially evaporated and purified on a Diaion HP20SS resin column (100 ml) using a gradient of methanol/water with acetic acid (1%). Fractions containing the desired product were combined and evaporated and the residue taken up in the minimum volume of methanol and further precipitated with ether and dried to give the desired compound.

Variations in the time taken for the condensation reaction of between 15 minutes to 2.75 hours were noted, depending on the reactants, and also the time required for hydrolysis of the acetoxy groups varied between 3.5 and 18 hours.

Particulars of the compounds prepared and the yields thereof are given in Table III, and the NMR characterising data is given in Table IV.

TABLE III

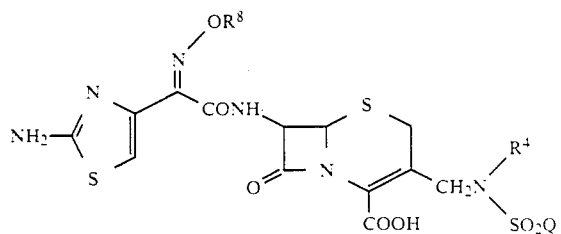

(AcO = CH$_3$COO—)

| Example No. | R$^8$ | R$^4$ | Q | Yield | Footnotes |
|---|---|---|---|---|---|
| 85 | —CMe$_2$CO$_2$H | H | naphthalene-2,3-diol | 35 |  |
| 86 | —C$_2$H$_5$ | H | naphthalene-2,3-diol | 47 |  |
| 87 | —CMe$_2$CO$_2$H | H | catechol | 45 |  |
| 88 | —C$_2$H$_5$ | H | catechol | 53 |  |
| 89 | cyclobutyl-COOH | —C$_2$H$_5$ | catechol | 15 | 1 |

TABLE III-continued
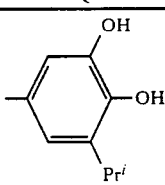
(AcO = CH₃COO—)
| Example No. | $R^8$ | $R^4$ | Q | Yield | Footnotes |
|---|---|---|---|---|---|
| 90 | —CMe₂CO₂H | H | 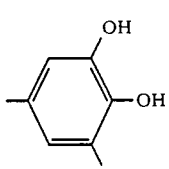 | 25 | 2 |
| 91 | —CMe₂CO₂H | H | 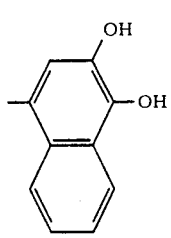 | 30 | 3 |
| 92 | —CMe₂CO₂H | H | 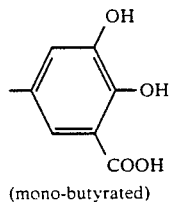 | 17 | 3,4 |
| 93 | —CMe₂CO₂H | H | 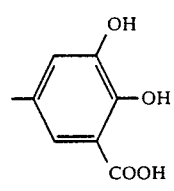<br>(mono-butyrated) | 21 | 4,5 |
| 94 | —CMe₂CO₂H | H | 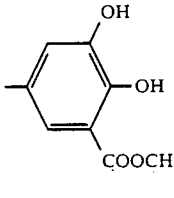 | 27 | 4,6 |
| 95 | —CMe₂CO₂H | H | 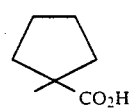 | 37 | 3,4,7 |
| 96 | 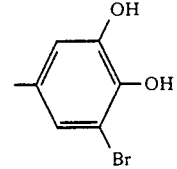 | H |  | 55 | 3,8 |

TABLE III-continued (AcO = CH₃COO—)

| Example No. | R⁸ | R⁴ | Q | Yield | Footnotes |
|---|---|---|---|---|---|
| 97 | —CMe₂CO₂H | H | (naphthalene with Br, OAc, OAc, Br, methyl) | 19 | 9 |
| 98 | —CMe₂COOH | H | (naphthalene with Cl, OAc, OAc, Cl, methyl) | 38 | 4,10 |
| 99 | —CMe₂COOH | H | (naphthalene with Cl, OH, OH, Cl, methyl) | 18 | 11 |

Footnotes to Table III
1. The product was purified by HPLC on an octadecylsilane column by gradient elution with methanol/water with acetic acid (1%) and then further freeze dried.
2. The product was purified on a Diaion HP20SS resin column followed by HPLC on an octadecylsilane column (in both purifications the eluting system was MeOH/H₂O with 1% AcOH).
3. Cleavage of the protecting groups was performed with 10% NH₄OH.
4. Solvent used was dimethylformamide instead of acetone/water.
5. Starting material was 2-carboxylic acid-3,4-di-isobutyrate benzenesulphonyl chloride. Only one isobutyrate group cleaved on treatment with 10% NH₄OH in aqueous methanol. Reaction performed on 0.41 mmole cephalosporin with triethylamine (1.8 mmole).
6. Reaction performed on 0.6 mmole cephalosporin with 5 equivalents of triethylamine, at 70° C. Same starting material as Example 93. Both isobutyrate groups cleaved on treatment with 20% NH₄OH.
7. Reaction performed on 0.95 mmole cephalosporin with 4 equivalents of triethylamine, at −50° C. Starting material protected as di-isobutyrate.
8. Reaction performed on 0.54 mmole cephalosporin with 3 equivalents of triethylamine. Starting material protected as di-isobutyrate.
9. Reaction performed on 0.6 mmole cephalosporin with two and a half equivalents triethylamine.
10. Reaction performed on 1.24 mmole cephalosporin with 4 equivalents triethylamine at −50° C.
11. Hydrolysis of the compound of Example 98 at pH 8.0–8.3 with 5% NH₄OH followed by Diaion HP 20 SS resin chromatography using aqueous methanol containing hydrochloric acid (pH 3.7).

TABLE IV

NMR data for the compounds of Table III taken at 90 MHz in DMSOd₆ + CD₃CO₂D + TFAd.

| Example No. | delta values (ppm) |
|---|---|
| 85 | 1.53(s, 6H); 3.28(m, 2H); 3.4 to 4.2(m, 2H); 4.51 (d, 1H); 5.60(d, 1H); 7.03(s, 1H); 7.19(s, 1H); 7.26(s, 1H); 7.46(d, 1H); 7.68(d, 1H); 8.02(br. s, 1H). |
| 86 | 1.27(t, 3H); 3.34(br, s, 2H); 3.69(d, 1H); 4.10(d, 1H); 4.24(q, 2H); 4.61(d, 1H); 5.67(d, 1H); 6.99(s, 1H); 7.24(s, 1H); 7.30(s, 1H); 7.51(br, d, 1H); 7.75(d, 1H); 8.04(br, s, 1H). |
| 87 | 1.54(br, s, 6H); 3.40(m, 2H); 3.65(d, 1H); 4.00(d, 1H); 4.99(d, 1H); 5.79(d, 1H); 6.86(d, 1H); 7.07(s, 1H); 7.12(br, d, 1H); 7.18(brs, 1H). |
| 88 | 1.28(t, 3H); 3.42(br.s, 2H); 3.64(d, 1H); 3.99(d, 1H); 4.24(q, 2H); 4.97(d, 1H); 5.74(d, 1H); 6.87(d, 1H); 7.00(s, 1H); 7.13(br.d, 1H); 7.18(br.s, 1H). |
| 89 | 0.96(t, 3H); 1.8–2.1(m, 2H); 2.3–2.7(m, 4H); |
| 90 | 3.12(q, 2H); 3.32(d, 1H); 3.61(d, 1H); 4.01(d, 1H); 4.15(d, 1H); 5.25(d, 1H); 5.89(d, 1H); 6.91(d, 1H); 7.05(s, 1H); 7.11(dd, 1H); 7.14(d, 1H). 1.16(d, 6H); 1.56(br, s, 6H); 3.1–3.7(m, 1H); 3.43 (2H, br.s); 3.67(d, 1H); 4.03(d, 1H); 4.95(d, 1H); 5.77(d, 1H); 7.10(s, 3H). |
| 91 | 1.53(br.s, 6H); 3.42(brs, 2H); 3.67(d, 1H); 4.03(d, 1H); 4.96(d, 1H); 5.77(d, 1H); 7.07(s, 1H); 7.21(d, 1H); 7.37(d, 1H). |
| 92 | 1.54(br, s, 6H); 3.29(br.s, 2H); 3.66(d, 1H); 3.99(d, 1H); 4.87(d, 1H); 5.75(d, 1H); 7.05(s, 1H); 7.3–7.6(m, 2H); 7.87(s, 1H); 8.05–8.30(m, 1H); 8.35–8.60(m, 1H). |
| 93 | 1.22(s, 3H); 1.30(s, 3H); 1.55(br s, 6H); 2.92(m, 1H); |

TABLE IV-continued

NMR data for the compounds of Table III taken at 90 MHz in $DMSOd_6 + CD_3CO_2D + TFAd$.

| Example No. | delta values (ppm) |
|---|---|
|  | 3.50(m, 2H); 3.70-4.20(m, 2H); 5.01(d, 1H); 5.80(d, 1H); 7.08(br, 1H); 7.73(d, 1H); 8.15(d, 1H). |
| 94 | 1.54(s, 6H); 3.47(m, 2H); 3.68(d, 1H); 4.00(d, 1H); 5.03(d, 1H); 5.79(d, 1H); 7.07(s, 1H); 7.38(d, 1H); 7.71(d, 1H). |
| 95 | 1.55(s, 3H); 1.56(s, 3H); 3.46(m, 2H); 3.70(d, 1H); 4.00(d, 1H); 3.90(s, 3H); 5.00(d, 1H); 5.79(d, 1H); 7.08(s, 1H); 7.40(d, 1H); 7.70(d, 1H). |
| 96 | 1.5-2.5(m, 8H); 3.44(m, 2H); 3.71(d, 1H); 4.06(d, 1H); 4.99(d, 1H); 5.80(d, 1H); 7.08(s, 1H); 7.22(d, 1H); 7.36(d, 1H). |
| 97 | 1.54 (br s, 6H); 1.83(s, 6H); 3.53(br s, 2H); 3.77(d, 1H); 4.04(d, 1H); 5.01(d, 1H); 5.72(d, 1H); 7.05(s, 1H); 8.10(d, 1H); 8.49(d, 1H); 8.71(s, 1H). |
| 98 | 1.55(br s, 6H); 2.52(br s, 6H); 3.50(m, 2H); 3.77(d, 1H); 4.03(d, 1H); 4.98(d, 1H); 5.75(d, 1H); 7.06(s, 1H); 8.10(br d, 1H); 8.48(d, 1H); 8.72(br s, 1H). |
| 99 | 1.56(s, 6H); 3.49(m, 2H); 3.77(d, 1H); 4.08(d, 1H); 4.96(d, 1H); 5.77(d, 1H); 7.07(s, 1H); 7.83(br d, 1H); 8.20(d, 1H); 8.49(br s, 1H). |

EXAMPLES 100-104

The following general procedure was used for the preparation of the compounds of Examples 100-104, of which particulars are given in Tables V and VI.

To a stirred solution of the appropriate 7-substituted 3-aminomethylceph-3-em-4-carboxylic acid (0.5 mmole) and triethylamine (1.75 mmole) in methanol (4 ml), at about $-17°$ C., was added a solution of the appropriate acyl chloride (0.6 mmole) in acetonitrile (0.5 ml). The solution was stirred at 0° C. for 1 hour, acidified with glacial acetic acid, and evaporated to give a residue. This was dissolved in water (10 ml) containing sodium acetate (1 g) and subjected to medium pressure chromatography on HP 20 SS resin gradient eluting with aqueous acetonitrile (twice). The desired product was isolated by partially evaporating the appropriate fractions, freeze drying, triturating with acetone and drying under vacuum.

TABLE V

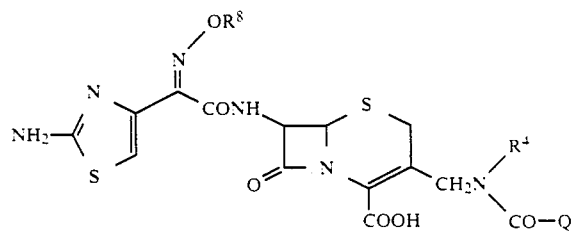

| EXAMPLE NO. | $R^8$ | $R^4$ | Q | YIELD (%) | FOOTNOTE |
|---|---|---|---|---|---|
| 100 | $-CMe_2COOH$ | H | (pyranone with OAc) | 25 |  |
| 101 | $-CH_2CH_3$ | H | (pyranone with OAc) | 41 | 1,2,3 |
| 102 | $-CMe_2COOH$ | H | (pyranone with OH, OH) | 39 | 3,4 |
| 103 | $-CMe_2COOH$ | H | (pyranone with OAc, OH) | 12 | 3,5 |

TABLE V-continued

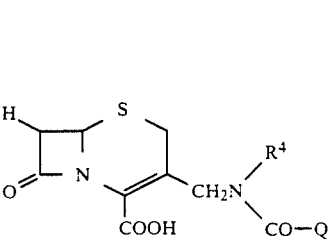

| EXAMPLE NO. | $R^8$ | $R^4$ | Q | YIELD (%) | FOOTNOTE |
|---|---|---|---|---|---|
| 104 | —$CH_2CH_3$ | H | 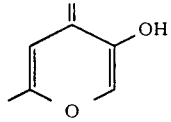 | 76 | 6 |

FOOTNOTES TO TABLE V

1. The reaction was performed in dimethylformamide. Triethylamine (1.25 m mole) was present. The starting material was insoluble initially but dissolved upon reaction. Product isolated as triethylamine salt.
2. Only one MPLC column required.
3. Not triturated after freeze drying.
4. Triethylamine (2.25 mmole) and dihydroxy acyl chloride (0.75 mmole) used.
5. 1 mmole scale. Diacetoxy acylchloride reacted; partial deprotection due to pH of medium.
6. To a stirred suspension of the product of Example 101 (0.21 mmole) in water (3 ml) was added 0.5 M aqueous ammonium hydroxide to take the pH to 8.4. The solution was maintained at this pH for 2 hours and acidified to pH 2 with dilute hydrochloric acid. The precipitate was collected by filtration, washed with water and dried to give the desired product.

TABLE VI

NMR data for the compounds of Table V taken at 200 MHz in DMSO $d_6$ + $CD_3CO_2D$.

| Example No. | delta values (ppm) |
|---|---|
| 100 | 1.43 (d, 6H); 2.24(s, 3H); 3.48(q, 2H); 4.28(q, 2H); 5.07(d, 1H); 5.78(d, 1H); 6.74(s, 1H); 6.97(s, 1H); 8.48(s, 1H). |
| 101 | 1.17(m, 12H); 2.21(s, 3H); 3.06(q, 6H); 3.48(q, 2H); 4.07(q, 2H); 4.29(q, 2H); 5.06(d, 1H); 5.75(d, 1H); 6.71(s, 1H); 6.96(s, 1H); 8.40(s, 1H). |
| 102 | 1.43(d, 6H); 3.50(q, 2H); 4.25(q, 2H); 5.09(d, 1H); 5.82(d, 1H); 6.74(s, 1H); 6.88(s, 1H). |
| 103 | 1.44(2s, 6H); 2.21(s, 3H); 3.49(q, 2H); 4.25(q, 2H); 5.10(d, 1H); 5.82(d, 1H); 6.74(s, 1H); 6.87(s, 1H). |
| 104 | 1.22(t, 3H); 3.50(q, 2H); 4.12(q, 2H); 4.29(q, 2H); 5.08(d, 1H); 5.76(d, 1H); 6.80(s, 1H); 6.89(s, 1H); 8.06(s, 1H). |

EXAMPLES 105-115

The following general procedure was used for the preparation of the compounds of Examples 105-115, of which particulars are given in Tables VII and VIII. In these Examples a 3-aminomethylceph-3-em-4-carboxylic acid is coupled with an active ester of an acid to form the desired 3-substituted amino methyl cephalosporin.

A solution of the active ester was prepared by dissolving the parent acid (1 equivalent) in dimethylsulphoxide or dichloromethane and adding hydroxysuccinimide (1 equivalent). To this solution, at 0° C., was added dicyclohexylcarbodi-imide (1 equivalent) and the resultant mixture was stirred for up to 3 hours. The solid, dicyclohexylurea, was removed by filtration and the solution of the active ester was either used as it was or was evaporated in vacuo.

To a solution of the appropriate 7-substituted 3-aminomethylceph-3-em-4-carboxylic acid (1 equivalent) was added triethylamine (1-3 equivalents) and a solution of the active ester (1 equivalent). The reaction mixture was stirred for up to 20 hours (monitoring progress by HPLC), diluted with water and acidified with excess acetic acid. If necessary sodium acetate was added to dissolve the crude solid product. The resultant solution was subjected to chromatography on HP 20 SS resin eluting with acetonitrile/water mixtures containing acetic acid (1%).

TABLE VII

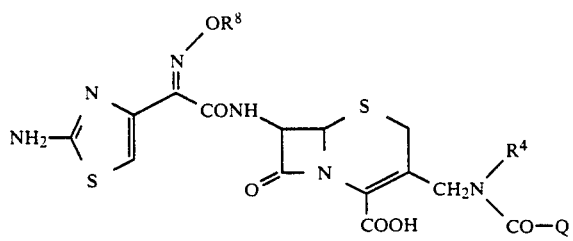

| EXAMPLE NO. | R⁸ | R⁴ | Q | YIELD (%) | FOOTNOTE |
|---|---|---|---|---|---|
| 105 | —CMe₂COOH | H | 3-benzyloxy-2-methyl-4-oxo-1-pyridinyl-CH₂CH₂— | 66 | 1 |
| 106 | —CH₂CH₃ | H | 3-benzyloxy-2-methyl-4-oxo-1-pyridinyl-CH₂CH₂N | 47 | 1,2 |
| 107 | —CMe₂COOH | H | 3-hydroxy-2-methyl-4-oxo-1-pyridinyl-CH₂CH₂— | 31 | 3 |
| 108 | —CMe₂COOH | H | 3-hydroxy-6-methyl-4-oxo-1-pyridinyl | 31 | 4,8 |
| 109 | —CH₂CH₃ | H | 3-OAc-4-OH-6-methyl-pyridinyl | 8 | 4,5,6 |
| 110 | 1-carboxycyclopentyl | H | 3-hydroxy-6-methyl-4-oxo-1-pyridinyl | 12 | 4,5 |
| 111 | 1-carboxycyclobutyl | H | 3-hydroxy-6-methyl-4-oxo-1-pyridinyl | 19 | 4,5 |
| 112 | —CMe₂COOH | H | 3-bromo-4,5-dihydroxy-2-methyl-pyridinyl | 18 | 4,9 |

TABLE VII-continued

[Structure: 2-aminothiazole with =N-OR8 oxime, CONH linked to β-lactam/cephem with COOH and CH2N(R4)(CO-Q) substituent]

| EXAMPLE NO. | $R^8$ | $R^4$ | Q | YIELD (%) | FOOTNOTE |
|---|---|---|---|---|---|
| 113 | —CMe₂COOH | H | 3-Br-4-OH-5-OCH₂Ph-6-methylpyridine | 78 | 4,7 |
| 114 | —CMe₂COOH | H | 2,3,4-triOH-6-methylpyridine | 22 | 4 |
| 115 | —CH₂CH₃ | H | 2,3,4-triOH-6-methylpyridine | 18 | 4,8 |

FOOTNOTES TO TABLE VII

1. Active ester formed on 3.09 mmole scale in dichloromethane (10 ml). Coupling reaction performed on 1.55 mmole scale, with 2.1 equivalents of triethylamine and cephem, in dimethylformamide (10 ml)/dichloromethane (5 ml), for 20 hours. On completion of reaction the mixture was filtered, the volume of solvent reduced by use of a 'cold-finger' evaporator and aqueous methanol (1:1) containing trifluoroacetic acid (0.2%) was added. The beige precipitate was redissolved with sodium acetate, filtered and subjected to chromatography.
2. Dimethylsulphoxide (2 ml) added to aid solubility of cephalosporin starting material.
3. Treatment of the compound of Example 105 with trifluoroacetic acid for 30 hours gave the deprotected product and unchanged starting material (1:1) which were separated by chromatography on HP 20 SS resin.
4. Coupling reaction performed on 0.5 mmole scale, in dimethyl-sulphoxide (3 ml).
5. Coupling performed on diacetoxy compound. Product isolated by adjusting pH of reaction mixture to 8.4 with aqueous ammonia followed by HPLC.
6. 29% of product was dihydroxy compound formed by deacetylation.
7. Debenzylation of Example 113 carried out in trifluoroacetic acid, for 18 hours, in the presence of anisole and thioanisole (5 equivalents each). Purified on HP 20 SS resin and by Dynamax reverse phase preparative HPLC.
8. Coupling performed on unprotected hydroxy acyl compounds.
9. Coupling performed on mono benzyloxy compound.

TABLE VIII

NMR data for the compounds of Table VII taken at 200 MHz in DMSO-d₆/CD₃CO₂D.

| Example No. | delta values (ppm) |
|---|---|
| 105 | 1.43 and 1.45(2s, 6H); 2.3(s, 3H); 2.58(t, 2H); 3.36(q, 2H); 4.05(q, 2H); 4.27(t, 2H); 5.0(s, 2H); 5.08(d, 1H); 5.84(d, 1H); 6.55(d, 1H); 6.76(s, 1H); 7.3–7.45(m, 5H); 7.75(d, 1H). |
| 106 | 1.2(t, 3H); 2.24(s, 3H); 2.57(t, 2H); 3.36(q, 2H); 4.05(q, 2H); 4.08(q, 2H); 4.15(t, 2H); 5.0(s, 2H); 5.06(d, 1H); 5.75(d, 1H); 6.32(d, 1H); 6.73(s, 1H); 7.28–7.44(m, 5H); 7.6(d, 1H). |
| 107 | 1.4–1.5(d, 6H); 2.4(s, 3H); 2.6–2.7(br m, 2H); 3.15–3.5(q, 2H); 3.8–4.3(q, 2H); 4.2–4.35 (br m, 2H); 5.05(d, 1H); 5.85(d, 1H); 6.5(d, 1H); 6.75(s, 1H); 7.65(d, 1H). |
| 108 | 1.4(d, 6H); 3.4–3.7(q, 2H); 3.9–4.5(q, 2H); 5.1(d, 1H); 5.8(d, 1H); 6.75(s, 1H); 7.45(s, 1H); 7.9(s, 1H). |
| 109 | 1.15–1.25(t, 3H); 2.25(s, 2.13H); 3.35–3.7 (q, 2H); 3.95–4.15(m, 3H); 4.4–4.5(d, 1H); 5.1(d, 1H); 5.75(d, 1H); 6.7(s, 1H); 7.4(s, 0.29H); 7.55(s, 0.71H); 7.9(s, 0.29H); 8.1(s, 0.71H). |
| 110 | 1.5–1.8(br m, 4H); 1.95–2.2(br m, 4H); 3.4–3.7(q, 2H); 3.9–4.5(q, 2H); 5.1(d, 1H); 5.8(d, 1H); 6.75(s, 1H); 7.4(s, 1H); 7.9(s, 1H). |
| 111 | 1.75–1.9(m, 2H); 2.2–2.5(br m, 4H); 3.4–3.7(q, 2H); 3.9–4.5(q, 2H); 5.1(d, 1H); 5.8(d, 1H); 6.75(s, 1H); 7.4(s, 1H); 7.9(s, 1H). |
| 112 | 1.45(d, 6H); 3.45–3.75(q, 2H); 4.05–4.5(q, 2H); 5.15(d, 1H); 5.8(d, 1H); 6.8(s, 1H); 7.6(s, 1H). |
| 113 | 1.45(d, 6H); 3.4–3.7(q, 2H); 4.0–4.5(q, 2H); 5.1–5.2(m, 3H); 5.8(d, 1H); 6.7(s, 1H); 7.25–7.45(m, 5H); 7.7(s, 1H). |
| 114 | 1.16(t, 9H); 1.46(2s, 6H); 3.08(q, 6H); 3.50(q, 2H); 4.24(q, 1H); 5.11(d, 1H); 5.82(d, 1H); 6.74(s, 1H); 6.86(s, 1H). |
| 115 | 1.19 (m, 12H); 3.08(q, 6H); 3.49(q, 2H); 4.08(q, merged); 4.24(q, merged); 5.09(d, 1H); 5.76(d, 1H); 6.71(s, 1H); 6.83(s, 1H). |

EXAMPLES 116–118

The following general procedure was used for the preparation of the compounds of Examples 116–118, of which particulars are given in Tables IX and X. An active ester with succinimide is formed as in Examples 105–115 (Table VII) and coupled to a 3-aminomethyl-ceph-3-em-4-carboxylic acid in a similar manner. The appropriate cephalosporin (0.5 mmole) was dissolved in water (4 ml) containing sodium bicarbonate (1.5 mmole) and the appropriate active ester (0.5 mmole) in acetonitrile (2 ml) was added. The reaction was stirred at room temperature for 2 hours, evaporated to dryness, the residue was taken up in trifluoroacetic acid (10 ml) and allowed to stand for 1 hour. The solvent was evaporated and the residue purified on HP 20 SS resin eluting with acetonitrile/water mixtures containing acetic acid (1%). The trifluoroacetic acid deprotection step was omitted in Example 118.

TABLE IX

[Structure: 2-aminothiazole-oxime-cephalosporin with $OR^8$, CONH, COOH, $CH_2-N(R^4)-CO-Q$ substituents]

| EXAMPLE NO. | $R^8$ | $R^4$ | Q | YIELD (%) |
|---|---|---|---|---|
| 116 | [cyclobutyl with COOH] | H | $-\overset{NH_2}{\underset{|}{CH}}-CH_2-$[phenyl with OH, OH] | 50 |
| 117 | $-CH_2CH_3$ | H | $-\overset{NH_2}{\underset{|}{CH}}-CH_2-$[phenyl with OH, OH] | 42 |
| 118 | [cyclobutyl with COOH] | H | $-\overset{NHCOCH_3}{\underset{|}{CH}}-CH_2-$[phenyl with OH, OH] | 84 |

TABLE X

NMR data for the compounds of Table IX taken at 200 MHz in DMSO-$d_6$/CD$_3$CO$_2$D.

| Example No. | delta values (ppm) |
|---|---|
| 116 | 1.8(obscured); 2.3-2.5(m, 4H); 2.7-2.9(m, 2H); 3.05-3.45(q, 2H); 3.8-4.0(m, 3H); 4.25-4.4(d, 1H); 5.05-5.1(d, 1H); 5.8-5.9(d, 1H); 6.4-6.5(q, 1H); 6.6(d, 1H); 6.6-6.7(d, 1H); 6.8(s, 1H). |
| 117 | 1.15-1.3(t, 3H); 2.7-2.9(m, 2H); 3.05-3.45(q, 2H); 3.8-4.0(m, 3H); 4.0 4.2(q, 2H); 4.25-4.4(d, 1H); 5.05(d, 1H); 5.75(d, 1H); 6.4-6.5(q, 1H); 6.6(d, 1H); 6.65-6.7(d, 1H). |
| 118 | 1.75-1.8(m, 2H); 2.25-2.5(br m, 4H); 2.7-2.75 (m, 2H); 3.2-3.5(m, 2H); 3.8-4.0(m, 2H); 4.2(m, 1H); 4.3-4.45(m, 2H); 5.1(m, 1H); 5.85(d, 1H); 6.4-6.5(m, 1H); 6.55-6.65(m, 2H). |

EXAMPLES 119–124

The following general procedure was used for the preparation of the compounds of Examples 119–124, of which particulars are given in Tables XI and XII.

To a suspension of the appropriate 7-substituted 3-aminomethylceph-3-em-4-carboxylic acid in methanol, at 0° C., was added rapidly, triethylamine (2–3 equivalents) followed by the appropriate protected carbonyl chloride or derivative thereof in a minimum amount of dichloromethane. After up to 2 hours, at room temperature, the mixture was acidified, evaporated and the residue purified on Diaion HP 20 SS resin using aqueous methanol containing acetic acid (1%) as eluent.

TABLE XI

[Structure: 2-aminothiazole-oxime-cephalosporin with $OR^8$, CONH, COOH, $CH_2-N(R^4)-CO-Q$ substituents]

| EXAMPLE NO. | $R^8$ | $R^4$ | Q | YIELD (%) | FOOTNOTE |
|---|---|---|---|---|---|
| 119 | $-CH_2CH_3$ | H | $CH_2OAc$ [phenyl with OH] | 38 | 1,2 |
| 120 | $-CH_2CH_3$ | H | $CH_2CN$ [phenyl with OH] | 12 | 3 |

TABLE XI-continued

[Structure: 2-aminothiazole with OR⁸ oxime, linked via CONH to cephem nucleus with CH₂-N(R⁴)-CO-Q substituent at 3-position]

| EXAMPLE NO. | R⁸ | R⁴ | Q | YIELD (%) | FOOTNOTE |
|---|---|---|---|---|---|
| 121 | —CMe₂COOH | H | (2-CH₂OH, 3-OH phenyl, methyl-substituted) | 11 | 2,4 |
| 122 | —CH₂CH₃ | H | (2-OAc, 3-COOCH₃ phenyl, methyl-substituted) | 44 | 5 |
| 123 | —CMe₂COOH | H | (2-COOH, 3-OH phenyl, methyl-substituted) | 16 | 6,7 |
| 124 | —CMe₂COOH | H | (2,3-dihydroxy naphthyl, methyl-substituted) | 20 | 2,8 |

FOOTNOTES TO TABLE XI
1. Reaction performed on 0.48 mmole of cephalosporin with 2 equivalents of triethylamine in methanol (10 ml). Potassium cyanide (0.05 g) added to reaction mixture after 15 minutes.

TABLE XII

NMR data for the compounds of Table XI taken at 90 MHz in DMSO-d₆/CD₃CO₂D/TFA-d.

| Example No. | delta values (ppm) |
|---|---|
| 119 | 1.28(t, 3H); 2.03(s, 3H); 3.50(m, 2H); 4.00-4.50 (m, 4H); 5.05(s, 2H); 5.13(d, 1H); 5.73(d, 1H); 6.87(d, 1H); 7.00(s, 1H); 7.69(br d, 1H); 7.77(brs, 1H). |
| 120 | 1.29(t, 3H); 3.45(d, 1H); 3.61(d, 1H); 3.84(s, 2H); 4.18(d, 1H); 4.45(d, 1H); 4.24(g, 2H); 5.16(d, 1H); 5.78(d, 1H); 6.92(d, 1H); 6.98(s, 1H); 7.72(dd, 1H); 7.82(d, 1H). |
| 121 | 1.54(s, 3H); 1.56(s, 3H); 3.48(d, 1H); 3.61(d, 1H); 4.19(d, 1H); 4.43(d, 1H); 5.18(d, 1H); 5.83(d, 1H); 6.83(d, 1H); 7.07(s, 1H); 7.63(dd, 1H); 7.89(d, 1H). |
| 122 | 1.27(t, 3H); 2.26(s, 3H); 3.52(m, 2H); 3.80(s, 3H); 4.23(q, 2H); 4.16(d, 1H); 4.53(d, 1H); 5.14(d, 1H); 5.75(d, 1H); 7.00(s, 1H); 7.27(d, 1H); 8.12(dd, 1H); 8.42(d, 1H). |
| 123 | 1.55(s, 6H); 3.54(m, 2H); 4.18(d, 1H); 4.48(d, 1H); 5.16(d, 1H); 5.79(d, 1H); 6.97(d, 1H); 7.07(s, 1H); 8.00(dd, 1H); 7.37(d, 1H). |
| 124 | 1.53(s, 6H); 3.57(m, 2H); 4.27(d, 1H); 4.50(d, 1H); 5.16(d, 1H); 5.81(d, 1H); 7.08(s, 1H); 7.15(s, 1H); 7.21(s, 1H); 7.61(s, 2H); 8.14(s, 1H). |

EXAMPLE 125

7-(2-Thienylacetamido)-3-(3,4-diacetoxybenzoyloxymethyl)ceph-3-em-4-carboxylic acid.

To a solution of diphenylmethyl 7-(2-thienylacetamido)-3-hydroxymethylceph-3-em-4-carboxylate (2.08 g, $4 \times 10^{-3}$ mole) and 3,4-diacetoxybenzoyl chloride (5.12 g, $2 \times 10^{-2}$ mole) in THF(50 ml) was added pyridine (1.6 ml, $2 \times 10^{-2}$ mole) at room temperature. Stirring was continued at room temperature for 1.5 h. Precipitated pyridinium hydrochloride was filtered off and the residue chromatographed over $SiO_2$ (100 g), eluting with $CH_2Cl_2$/MeOH, 98/2. After evaporation of the solvent, the product was precipitated in ether, to obtain 2.1 g (71%) of diphenylmethyl 7-(2-thienylacetamido)-3-(3,4-diacetoxy) benzoyloxymethyl-ceph-3-em-4-carboxylate, Nmr (DMSO/AcOD) 2.3 (s,6H); 3.8(m,4H); 3.9-4.1(m,2H); 5.2(d,1H); 5.8(d,1H); 7(s,1H); 7-8(m,16H).

A solution of 100 mg ($0.135 \times 10^{-3}$ mole) of the above compound in TFA (1 ml) and anisole (0.5 ml) was stirred at room temperature for 1.5 h. After evaporation of the solvents, the mixture was triturated in a pentane-ether mixture to yield 43 mg (56%) of the title compound, Nmr (DMSOd₆, AcOD, TFA) 2.25(s,6H); 3.6-3.9(m,4H); 5.2(m,2H); 5.1(d,1H); 5.75(d,1H); 7(s,1H); 6.95(d,1H); 7.3(dd,1H); 7.9(d,1H).

EXAMPLE 126

7-[2-(2-Aminothiazol-4-yl)-2-(Z)-1-carboxy-1-methylethoxyimino)-acetamido]-3-(3,4-dihydroxybenzoyloxymethyl)ceph-3-em-4-carboxylic acid was prepared as follows:

To a mixture of diphenylmethyl 7-(2-thienylacetamido)-3-(3,4-diacetoxybenzoyloxymethyl)-ceph-3-em-4-carboxylate (1.8 g, $2.4 \times 10^{-3}$ and pyridine (0.590 ml, $7.3 \times 10^{-3}$ mole) in anhydrous $CH_2Cl_2$ at $-20°$ C. was added $PCl_5$ (1.01 g, $4.8 \times 10^{-3}$ mole).

After 15 min at $-20°$ C. the mixture was allowed to reach room temperature and was stirred for 1.5 h. The solution was then again cooled to $-20°$ C. and butane-1,3-diol (1.1 ml, $1.15 \times 10^{-2}$ mole) in 10 ml $CH_2Cl_2$ was added. The mixture was allowed to reach room temperature in 1 h, the $CH_2Cl_2$ was evaporated, and the residue was triturated in ether. The gum thus obtained was purified by rapid $SiO_2$ chromatography ($CH_2Cl_2$/MeOH 98/2) and the fractions containing the desired product were put together, HCl in ether added and the product, diphenylmethyl 7-amino-3-(3,4-diacetoxybenzoylmethyl)-ceph-3-em-4-carboxylate hydrochloride (730 mg 50%) precipitated out. NMR $DMSOd_6+AcOD+TFAd$ 2.3(s,6H); 3.8(m,2H); 5-5.2(m,2H); 5.3(s,2H); 7(s,1H).

The corresponding free base was then obtained by treating the hydrochloride salt with TEA in MeOH at room temperature.

A solution of the said free base, 7-amino-3-(3,4-diacetoxy benzoyloxy)-ceph-3-em)4-carboxylate (500 mg, $0.76 \times 10^{-3}$ mole) together with 2-[(Z)-1-(t-butoxycarbonyl)-1-methylethoxyimino]-2-(2-tritylamino-thiazol-4-yl) acetic acid (519 mg, $0.91 \times 10^{-3}$ mole) and EEDQ (207 mg, $0.83 \times 10^{-3}$ mole) in $CH_2Cl_2$ (10 ml) was stirred at room temperature for 5 h. The solvent was evaporated, and the residue triturated in pentane, the solid rapidly chromatographed over $SiO_2$ (100 g) with $CH_2Cl_2$/MeOH 98.5/1.5 to yield 860 mg (94%) of diphenylmethyl 7-[2-(2-tritylaminothiazol-4-yl)-2-(Z)-1-t-butoxycarbonyl-1-methylethoxyimino)acetamido]-3-(3,4-diacetoxy benzoyloxymethyl)ceph-3-em-4-carboxylate. NMR in $DMSOd_6+AcOD$: 1.35(s,9H); 1.4(s,6H); 2.3(s,6H); 3.6-3.8(m,2H); 4.8-5.2(m,2H); 5.2(d,1H); 5.9(d,1H); 6.8(s,1H); 7(s,1H); 7-8(m,28H). A solution of the compound thus obtained (480 mg, $0.35 \times 10^{-3}$ mole) in a mixture of TFA (2 ml) and water (0.5 ml) was stirred at room temperature for 2 hrs. The solution was evaporated and the residue triturated in ether and filtered to yield 250 mg of the desired compound (crude) which was treated with $NaHCO_3$ (90 mg, $1.06 \times 10^{-3}$ mole) in a mixture of MeOH/$H_2O$ 50/50 (4 ml) for 1 hr at room temperature. The solvent was evaporated and the residue purified by preparative HPLC using MeOH/$(NH_4)_2 CO_3$ buffer (20/80). 52 mg (24%) of the title compound were obtained. NMR in $DMSOd_6$/ACoD/TFA 1.56(s,6H); 3.7(m,2H); 5.1(m,2H); 5.2(d,1H); 5.9(d,1H); 7.04(s,1H); 6.8(d,1H); 7.35(dd,1H); 7.38(d,1H).

EXAMPLES 127–131

In the same general manner as described for Examples 1–84 the following compounds were prepared.

TABLE XIII

| Example No. | $R^8$ | $R^4$ | Q | Yield (%) | Footnotes |
|---|---|---|---|---|---|
| 127 | —$CMe_2CO_2H$ | —$CH_2CH_3$ | 3,4-dihydroxy-5-fluorophenyl (HO, OH, F) | 32 | |
| 128 | —$CMe_2CO_2H$ | H | 2-fluoro-3,6-dihydroxy-5-fluorophenyl (F, OH, OH, F) | 25 | |
| 129 | —$CMe_2CO_2H$ | —$CH_2CH_3$ | 2-fluoro-3,6-dihydroxy-5-fluorophenyl (F, OH, OH, F) | 15 | |
| 130 | —$CH_2CH_3$ | H | 2-fluoro-3,6-dihydroxy-5-fluorophenyl (F, OH, OH, F) | 22 | |

TABLE XIII-continued

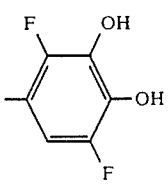

| Example No. | R⁸ | R⁴ | Q | Yield (%) | Footnotes |
|---|---|---|---|---|---|
| 131 | —CH$_2$CH$_3$ | —CH$_2$CH$_3$ | ![F,OH,OH,F benzene] | 12 | |

TABLE XIV

NMR data for the compounds of Table XIII taken at 90 MHz in DMSOd$_6$/CD$_3$CO$_2$D/TFAd.

| Example No. | Delta values (ppm) |
|---|---|
| 127 | 1.0(m, 3H); 1.55(s, 6H); 3.0–3.75(m, 4H); 4.0–4.75(m, 2H); 5.15(d, 1H); 5.85(d, 1H); 6.4(dd, 1H); 6.6(dd, 1H); 7.05(s, 1H). |
| 128 | 1.55(s, 6H); 3.6(m, 2H); 4.3(dd, 2H); 5.15(d,1H); 5.8(d, 1H); 6.75–7.25(m, 2H). |
| 129 | 1.0(m, 3H); 1.55(s, 6H); 3.0–3.6(m, 4H); 4.0–4.75(m, 2H); 5.25(d, 1H); 5.85(d, 1H); 6.65(dd, 1H); 7.05(s, 1H). |
| 130 | 1.25(t, 3H); 3.6(m, 2H); 4.0–4.6(m, 4H); 5.2(d, 1H); 5.75(d, 1H); 7.0(m, 2H). |
| 131 | 0.75–1.5(m, 6H); 2.9–3.8(m, 4H); 4.0–4.75(m, 4H); 5.15(d, 1H); 5.75(d, 1H); 6.7(dd, 1H); 7.0(s, 1H). |

PREPARATION OF STARTING MATERIALS

Cephalosporins

Reference may be made to EP-A 127992 and EPA 164944 for general descriptions of methods suitable for the preparation of cephalosporin starting materials. The starting materials for the Examples of the present invention are specifically described in EPA 164944.

Carbonyl Chlorides (Examples 1–84; 119–124)

The carbonyl chlorides (for reacting with the 3-aminomethyl cephalosporins) are prepared in conventional manner from the corresponding acid. Examples of conventional methods include:

(i) mixing the acid with phosphorus pentachloride (one equivalent) and heating to 90° C. for about 1 hour. Cooling the reaction mixture and evaporating (optionally azeotroping with toluene) gives material usable in a subsequent reaction.

(ii) Mixing oxalyl chloride and dimethylformamide in dichloromethane, at 0° C., for 1 hour. Adding the appropriate acid, stirring for a further hour at room temperature and evaporating gives material usable in a subsequent reaction.

(iii) Heating the acid with oxalyl chloride in toluene for 1 hour, at 90° C., cooling and evaporating.

(iv) Treating the acid with thionyl chloride.

Prior to formation of the acid chloride the hydroxy groups are protected in conventional manner, for example as acetoxy, benzyloxy or isobutyroxy derivatives.

Further details of the specific acids used for preparing the protected acid chlorides, used in the foregoing Examples, are given below:

TABLE

| ACID HOOC—X | USED FOR PREPARATION OF CHLORIDE OF EXAMPLE | COMMENTS AND REFERENCES |
|---|---|---|
| ![benzene with 2 OH] | 1, 5, 6, 8, 12, 33, 24, 25, 28, 29, 30 | Commercially available |
| ![benzene with HO, OH] | 2, 9 | Commercially available |

TABLE-continued

| ACID HOOC—X | USED FOR PREPARATION OF CHLORIDE OF EXAMPLE | COMMENTS AND REFERENCES |
|---|---|---|
| 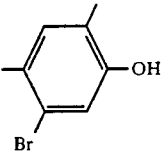 | 3, 10 | Dictionary of Organic Compounds |
| 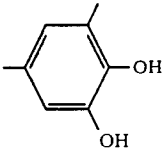 | 4, 7, 11 13, 16, 21 22 | Dictionary of Organic Compounds |
| 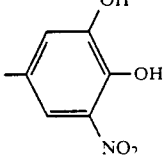 | 14, 15, 17 20, 38 | J. Antibiotics. 35, 1361 (1982) |
| 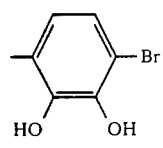 | 18, 19, 56, 61 | J. Org. Chem. 42(6)1068 (1977) |
| 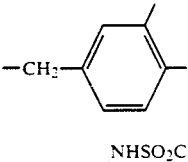 | 26, 27 | Commercially available |
| 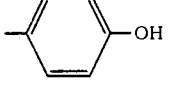 | 31 | 3-Amino-4-hydroxybenzoic acid in acetone was reacted with pyridine and methanesulphonyl chloride. |
| 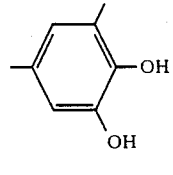 | 32 | Commercially available |
| 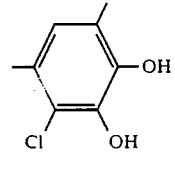 | 33, 51, 53 | Chlorination of 3,4-dihydroxybenzoic acid with chlorine in acetic acid. See also J. Antibiotics 40, 22 (1987). |
| 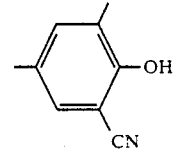 | 34, 35, 36, 41, 42 | Deprotection of 3-cyano-5-hydroxy-4-methoxybenzoic acid. J. Med. Chem. 25, 258 (1982). |

TABLE-continued

| ACID HOOC—X | USED FOR PREPARATION OF CHLORIDE OF EXAMPLE | COMMENTS AND REFERENCES |
|---|---|---|
| 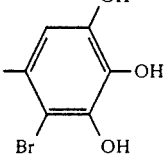 3-Br-4,5,6-tri-OH benzene | 37 | Bromination of gallic acid |
| 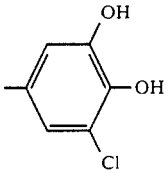 3-Cl-4,5-di-OH benzene | 39, 43 | J. Biol. Chem 258(23), 14413 (1983) |
| 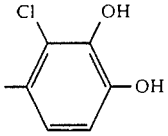 3-Cl-4,5-di-OH benzene | 40 | J. Biol. Chem., 258(23), 14413 (1983) |
| 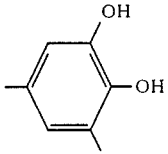 4-F-5,6-di-OH benzene | 44, 45, 47, 49 | J. Biol. Chem., 258(23), 14413 (1983) |
| 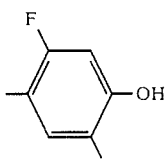 F, di-OH benzene | 46, 48 | Oxidation and deprotection of 3,4-dimethoxy-6-fluorobenzaldehyde. J. Org. Chem, 51(21), 4074 (1986) |
| 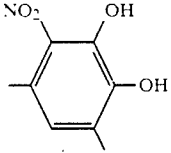 NO2, di-OH, Cl benzene | 50, 62 | Oxidation and deprotection of 5-chloro-4-hydroxy-3-methoxy-2-nitro benzaldehyde. J.A.C.S. 52, 4576 (1930) |
| 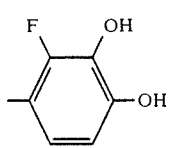 F, di-OH benzene | 52, 54, 59 | Oxidation and deprotection of 2-fluoro-3-hydroxy-4-methoxybenzalde-hyde. J. Org. Chem. 51(21), 4072 (1986). |
| 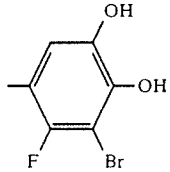 di-OH, F, Br benzene | 55, 58 | Bromination of the corresponding fluoro-dihydroxy benzoic acid above using bromine in acetic acid |
| 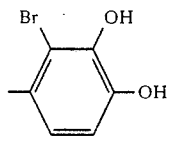 Br, di-OH benzene | 56 | Deprotection of 2-bromo-3-hydroxy-4-methoxybenzoic acid J.C.S. 2279 (1930). |

TABLE-continued

| ACID HOOC—X | USED FOR PREPARATION OF CHLORIDE OF EXAMPLE | COMMENTS AND REFERENCES |
|---|---|---|
| 3-Cl, 4-OH, 5-OH, 6-NO₂ benzoic acid | 57, 60 | Acetylation, nitration, oxidation and deprotection 2-chloro-3-hydroxy-4-methoxy benzaldehyde. J. Med. Chem., 29 (4), 2315 (1986) |
| 3-Br, 4-OH, 5-OH, 6-Br benzoic acid | 63, 65 | Bromination of 2-bromo-3,4-dihydroxy benzoic acid (see above) |
| 3-OH, 4-OH, 5-Br, 6-Br benzoic acid | 64 | Bromination of 2-bromo-4,5-dihydroxybenzoic acid. Dictionary of Organic compounds |
| 3-Br, 4-OH, 5-OH, 6-F benzoic acid | 66 | Bromination of 3-fluoro-4-5-dihydroxybenzoic acid (see above). |
| 3-HO, 4-OH, 6-F benzoic acid | 67, 127 | Deprotection of 2,3-dimethoxy-5-fluorobenzoic acid. Zh. Org. Khim. 20(3), 516 (1984). |
| —CH₂—(4-Br, 3-OH, 4-OH phenyl) | 68 | Demethylation of 2-bromo-4,5-dimethoxyphenylacetic acid using boron tribromide. J. Chem. Soc. 127, 1451 (1925). |
| —CH=CH—(2-Br, 4-OH, 5-OH phenyl) | 69, 76, 80, 81 | 2-Bromo-4,5-dimethoxybenzaldehyde(7.3 g), malonic acid (6.4 g), piperazine (0.5 ml) in pyridine (20 ml) at 110° C. for 3 hours. Cooled, poured into ice-water (250 ml), acidified (pH2). Precipitate removed. Residue stirred in aqueous sodium hydroxide (1 hour), filtered, acidified (pH2) to give desired precipitate. Deprotection of methoxy groups with BBr₃. |
| —CO—(3-OH, 4-OH phenyl) | 70 | |

| ACID HOOC—X | USED FOR PREPARATION OF CHLORIDE OF EXAMPLE | COMMENTS AND REFERENCES |
|---|---|---|
| 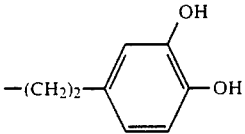 | 71 | |
| 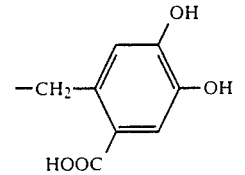 | 72, 82, 83 | Tetrahedron 31, 2607 (1965) |
| 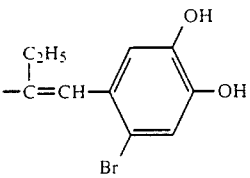 | 73 | As for the preparation of the acid (69 . . . ) above using ethyl malonic acid. |
| 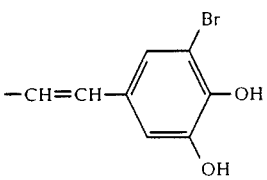 | 74 | As above using 3-bromo-4,5-dimethoxybenzaldehyde. |
| 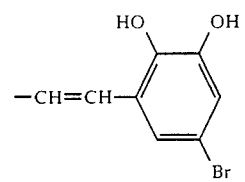 | 75 | As above using 5-bromo-2,3-dimethoxybenzaldehyde. |
| 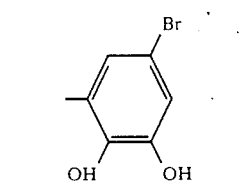 | 77, 78 79, 84 | J. Chem. Soc. 123, 1586 (1923) |
| 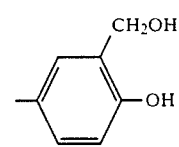 | 119 | 3-Methoxycarbonyl-4-hydroxy-benzoic acid (J.C.S. (1956) 4678) in diglyme was treated with lithium borohydride at 60° C. for 3 hours. Cooling, acidifying, extracting into $CH_2Cl_2$ and evaporating gave the product. |
| 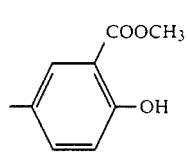 | 122 | J.C.S. (1956) 4678 |

TABLE-continued

| ACID HOOC—X | USED FOR PREPARATION OF CHLORIDE OF EXAMPLE | COMMENTS AND REFERENCES |
| --- | --- | --- |
| (benzene with COOH and OH) | 123 | N,N-Di-isopropyl-O-t-butylisourea (10 equivalents) and 5-formylsalicylic acid were stirred in ether for 3 days at 4° C. Filtered, washed (1N NaOH), evaporated and chromatographed to give 3-t-butylcarboxylate-4-t-butoxy-benzaldehyde. This was oxidised with potassium permanganate in acetone/water (containing 2 drops $H_2SO_4$). |
| (naphthalene with two OH) | 124 | 2,3-Dimethoxy-6-naphthoic acid (J. Het. Chem., 9, 805 (1972)) was stirred under reflux in concentrated HBr for 3 hours. Cooled and the desired product collected by filtration. |
| (benzene with F, OH, OH, F) | 128, 129, 130, 131 | 1,4-difluoro-2-methoxybenzene (J.O.C., 46, 203 (1981)) was converted to 2,5-difluoro-4-hydroxy-3-methoxy-benzaldehyde by the method described by Clark (J.O.C., 51, 4072 (1986)). Oxidation and deprotection gave the acid. |

In the above Table, general procedures of chlorination, bromination, oxidation and deprotection are mentioned. These are performed in standard manner. For example, chlorinations were performed by bubbling a slow stream of chlorine through a solution of the appropriate compound in acetic acid. When sufficient had been added the solution was degassed with a stream of nitrogen and the mixture evaporated to dryness to give crude product which was purified by standard techniques. Brominations were performed by adding one equivalent of bromine dropwise to a solution of the appropriate compound in acetic acid. The mixture was heated where necessary to complete the reaction and was then evaporated to dryness to give crude product which was purified by standard techniques. Oxidations were performed by adding to a suspension of freshly prepared $Ag_2O$ in water at 65° C., the appropriate aldehyde over 30 minutes. The precipitated silver was filtered off and the filtrate acidified and extracted with a suitable solvent to yield the crude acid. Deprotection (of methoxy groups) was performed by adding boron tribromide to a solution of the appropriate methoxy compound in dichloromethane at 0° C. After about 2 hours the mixture was carefully treated with ice and extracted with a suitable solvent to yield the crude product.

SULPHONYL CHLORIDES (EXAMPLES 85-99)

(A) 2,3-Diacetoxy-6-naphthalenesulphonyl chloride.

To a suspension of 2,3-dihydroxy-6-naphthalene sulphonic acid sodium salt (Aldrich) (2.62 g) in acetic anhydride (5 ml) was added four drops of concentrated sulphuric acid. The mixture was heated at 80° C. for 4 hours. After cooling, the crude mixture was taken up in dichloromethane followed by the addition of ether to precipitate 2,3-diacetoxy-6-naphthalene sulphonic acid (20 g; yield quantitative).

To a suspension of the crude 2,3-diacetoxy-6-naphthalenesulphonic acid (973 mg) in $CCl_4$ (3 ml) was added phosphorus pentachloride (750 mg). The mixture was heated at 80° C. for 20 minutes, cooled, and water added cautiously. The $CCl_4$ was separated from the aqueous layer and the latter was extracted with $CH_2Cl_2$. The organic extracts were combined, washed with water and dried over magnesium sulphate. Evaporation of the solvent yielded 2,3-diacetoxy-6-naphthalenesulphonyl chloride (160 mg, yield: 15%). NMR in $CDCl_3$: 2.37(s,6H); 7.82(s,1H); 7.87(s,1H); 7.99(s,1H); 8.01(s,1H); 8.54(br.s,1H).

(B) 3,4-Diacetoxybenzenesulphonyl chloride

Acetylation of 3,4-hydroxybenzene sulphonic acid (Beilstein EII, 11 p. 168) gave a product which was purified under the conditions described in A.

To a solution of the crude, 3,4-diacetoxy benzene sulphonic acid (0.83 g) in a mixture of sulpholane (1.5 ml) and acetonitrile (1.5 ml) was added at room temperature successively N,N-dimethylacetamide (75 μl), triethylamine (0.85 ml) and phosphorus oxychloride (1.1 ml). The reaction mixture was thereafter heated for 15 minutes at 70° C., cooled, poured onto water and extracted with $CH_2Cl_2$. The extract was dried over magnesium sulphate, concentrated and chromatographed on silica gel (50 g). Elution with $CH_2Cl_2$ gave 0.65 g (74%) of the title compound as a white solid. NMR in $CDCl_3$: 2.33(s,6H); 7.29(d,1H); 7.90(s,1H); 7.95(dd,1H).

(C) 1,2-Diacetoxy-3-isopropyl-5-benzenesulphonyl chloride

This compound was prepared in a manner analogous to that described in (A) starting with 1,2-dihydroxy-3-isopropyl benzene sulphonic acid which was synthesised as follows: 3 ml. concentrated sulphuric acid (98%) were added to 1,2-dihydroxy-3-isopropyl benzene and the mixture heated at 80° C. for 15 minutes. The mixture was cooled to 0° C. and water was added followed by 10 N NaOH to pH 5. Addition of ethanol to the solution left a precipitate which was filtered. The mother liquor was further evaporated, the crude mixture taken up in ethanol and the remaining solid removed. The solvent was evaporated and the residue was chromatographed on a column of Diaion HP20SS resin (350 ml). Elution with water gave 2.73 g (78%) of the expected sulphonic acid, NMR in DMSOd$_6$ 1.11(s,3H); 1.19(s,3H); 3.82(m,1H); 6.92(d,1H); 6.96(d,1H. NMR of the title compound in CDCl$_3$: 1.23(s,3H); 1.31(s,3H); 2.31(s,3H); 2.37(s,3H); 7.78(d,1H); 7.84(d,1H).

(D) 1,2-Diacetoxy-3-bromo-5-benzene sulphonyl chloride

A solution of bromine (0.75 ml) in acetic acid (10 ml) was added slowly over 30 minutes to a suspension of 1,2-dihydroxy-4-benzenesulphonic acid (2.7 g) in acetic acid (35 ml). The mixture was stirred for 15 hours at room temperature, the solid filtered and acetic acid evaporated. The residue was purified by chromatography on a column of Diaion HP20SS resin (950 ml). Elution with water yielded 1.15 g of 1,2-dihydroxy-3-bromo-benzene sulphonic acid. NMR in DMSOd$_7$: 7.08(d,1H); 7.16(d,1H). This derivative was thereafter acylated and treated with phosphorus oxychloride as described in the synthesis of B) to give the title compound, NMR in CDCl$_3$, 2.33(s,3H); 2.39(s,3H); 7.90(d,1H); 8.15(d,1H).

(E) 1,2-Diacetoxy-4-naphthalene sulphonyl chloride

Starting with 1,2-dihydroxy-4-naphthalene sulphonic acid (JACS 48, p. 1104, 1926) the procedure described under A) was used. NMR in DMSOd$_6$: 2.37(s,3H); 2.51(s,3H); 7.45–7.70(m,2H); 7.88(s,1H); 7.8–8.0(m,1H); 8.80–9.05(m,1H).

(F) 3-Carboxy-4,5-di-isobutyroxybenzene sulphonyl chloride

Concentrated sulphuric acid (1 ml) and 2,3-dihydroxybenzoic acid (0.5 g) were heated at 60° C. for 1 hour. The mixture was cooled, taken up in ether (20 ml), poured into dichloromethane (200 ml) and cooled to give as crystals, 3-carboxy-4,5-dihydroxybenzenesulphonic acid (0.31 g); δ(DMSO-d$_6$); 7.34(d,1H); 7.61(d,1H). To a suspension of this acid (1 g) in acetonitrile (10 ml) was added triethylamine (2.4 ml), followed by isobutyryl chloride (1.5 ml). The solution was stirred at room temperature for 1 hour, the solvent was evaporated and the residue purified by chromatography on Diaion HP 20 SS resin (aqueous methanol containing 1% acetic acid) to give 3-carboxy-4,5-di-isobutyroxy-benzene sulphonic acid (1.2 g); δ(DMSO-d$_6$): 1.19(s,6H); 1.27(s,6H); 2.90–3.15(m,2H); 7.63(d,1H); 8.04(d,1H).

Phosphorus pentachloride (0.75 g) was added to a suspension of the above sulphonic acid (0.6 g) in carbon tetrachloride (50 ml) and the mixture stirred under reflux for 4 hours. The solvent was evaporated, the residue taken up in ether, washed with water, dried and evaporated to give an oil. This oil was dissolved in acetone (30 ml), water (10 ml) added and the solution stirred for 2 hours. The solvents were evaporated; the residue was partitioned between ether (100 ml) and water (20 ml), the organic layer was dried and evaporated to give the title compound (0.21 g) as an oil; δ(CDCl$_3$): 1.30(s,6H); 1.38(s,6H); 2.50–3.20(m,2H); 8.15(d,1H); 8.66(d,1H).

(G) 3-Methoxy carbonyl-4,5-di-isobutyroxybenzene sulphonyl chloride

Concentrated sulphuric acid (4 ml) and 2,3-dihydroxybenzoic acid (1 g) were heated at 60° C. for 1 hour. Methanol (15 ml) was added and the solution stirred under reflux for a further 3 hours. The solvent was evaporated and the residue purified on Diaion HP 20 SS resin (aqueous methanol with 1% acetic acid) to give 3-methoxycarbonyl-4,5-dihydroxybenzene sulphonic acid (1.8 g); δ(DMSO-d$_6$); 3.88(s,3H); 7.32(d,1H); 7.57(d,1H). This was treated as in F (above) (chromatography on silica with methanol/dichloromethane as eluent) to give the title compound as a crystalline solid; δ(CDCl$_3$); 1.31(s,6H); 1.38(s,6H); 2.80–3.20(m,2H); 3.92(s,3H); 8.04(d,1H); 8.50(d,1H).

(H) 3-Bromo-4,5-di-isobutyroxybenzene sulphonyl chloride

3-Bromo-4,5-dihydroxybenzene sulphonic acid (see D on previous page) was treated successively with isobutyryl chloride and phosphorus pentachloride as in F above to give the title compound; δ(CDCl$_3$); 1.28(s,3H); 1.34(s,3H); 1.36(s,3H); 1.41(s,3H); 2.60–3.10(m,2H); 7.88(d,1H); 8.14(d,1H).

(I) 1,4-Dibromo-2,3-diacetoxy-6-naphthalene sulphonyl chloride

To a suspension of 2,3-dihydroxy-6-naphthalene sulphonic acid sodium salt (5.24 g) in acetic acid (100 ml) was added, dropwise over 30 minutes, bromine (2.3 ml) in acetic acid (50 ml). The solution was stirred at room temperature for 16 hours, partially concentrated and ether was added to precipitate 1,4-dibromo-2,3-dihydroxy-6-naphthalene sulphonic acid (8.7 g); δ(DMSO-d$_6$/TFA-d); 7.72(br d, 1H); 7.99(d,1H); 8.37(br s, 1H).

This was acetylated in conventional manner and treated with phosphorus pentachloride as in F (above) to give the title compound; δ(CDCl$_3$); 2.44(s,6H); 8.16(dd,1H); 8.56(d,1H); 9.02(d,1H).

(J) 1,4-Dichloro-2,3-diacetoxy-6-naphthalene sulphonylchloride

Chlorine was passed through a solution of 2,3-dihydroxy-6-naphthalene sulphonic acid sodium salt (2.0 g) in water (20 ml) until all starting material had been consumed. Solvent was evaporated and the residue purified by chromatography on Diaion HP 20 SS resin (aqueous methanol with 1% acetic acid) to give 1,4-dichloro-2,3-dihydroxy-6-naphthalene sulphonic acid.

This was acetylated in conventional manner and treated with phosphoris pentachloride as in F to give the title compound as a crystalline solid; δ(CDCl$_3$); 2.44 (s,6H); 8.16(dd,1H); 8.55(d,1H); 9.00(d,1H).

PYRANONE CARBONYL CHLORIDES (EXAMPLES 100-104)

(K) 2-Carboxy-5-hydroxypyran-4-one (20 mmole) (Chem.Abs., 1948,42,567; J. Gen. Chem., 1946,16, 2025), acetic anhydride (10 ml) and concentrated sulphuric acid (0.5 ml) were heated to reflux temperature. On cooling to 0° C., the 5-acetoxy compound crystallised (recrystallised from ethanol); δ(DMSO-d$_6$); 2.27(s,3H); 7.05(s,1H); 8.10(s,1H). This compound (5 mmole) was treated with oxalyl chloride (10 mmole) in dichloromethane (5 ml) containing dimethylformamide (15 μl). After 30 minutes the solvent was evaporated, the residue dissolved in toluene (evaporated several times to remove oxalyl chloride) and on final evaporation crystallised to give 5-acetoxypyran-4-one-2-carbonyl chloride which was used directly.

(L) In a manner similar to K above, 2-carboxy-5,6-dihydroxypyran-4-one (see reference in K) was converted to the corresponding di-acetoxy acid chloride. In an alternative the 2-carboxy-5,6-dihydroxypyran-4-one is directly treated with oxalyl chloride to form the corresponding dihydroxy acid chloride.

PYRIDINONE (ALKYL) CARBOXYLIC ACIDS (EXAMPLES 105-115)

As stated previously the acids are converted to active esters and used in situ.

(M) 1-Carboxyethyl-3-benzyloxy-4-hydroxy-2-methyl pyridinium chloride was prepared according to the method of EP-A 138421.

(N) 4,5-Diacetoxy pyridine-2-carboxylic acid was prepared by acetylation of 4,5-dihydroxypyridine-2-carboxylic acid.

(O) 5-Benzyloxy-3-bromo-4-hydroxypyridine-2-carboxylic acid was prepared by suspending 5-benzyloxy-4-hydroxy-2-carboxylic acid sodium salt (2.5 mmole; derived by benzylation of the corresponding dihydroxy compound) in 50% aqueous methanol (20 ml) and saturated $NaHCO_3$ was added to give complete solution. Bromine was added dropwise and the reaction mixture was stirred for 1 hour at room temperature. Solid crystallised; the mixture was cooled to complete crystallisation. The product was collected by filtration, washed with cold aqueous methanol and dried.

(P) 3,4,5-Trihydroxy pyridine-2-carboxylic acid was prepared according to the literature (see reference in K).

DOPAMINE DERIVATIVES (EXAMPLES 116-118)

As stated previously the acids are converted to active esters and used in situ.

(Q) L-Dopa (10 m mole) was suspended in 50% aqueous dioxan (75 ml) and treated with sodium bicarbonate (10 mmole) and di-t-butyl dicarbonate (11 mmole) and stirred for 18 hours. Further di-t-butyl dicarbonate (5 mmole) was added to complete the reaction. The dioxan was evaporated and the aqueous phase washed with ethyl acetate and acidified (in the presence of ethyl acetate) to pH 2-3. The organic phase was separated, washed, dried and evaporated to give t-butoxycarbonyl protected L-Dopa (75% yield); $\delta(CDCl_3)$; 1.4(s,9H); 2.8-3(d,2H); 4.2-4.5(m,1H); 6.4-6.6(q,1H); 6.65-6.8(m,2H).

(R) N-Acetyl L-Dopa was prepared according to the method of Helv. Chim. Acta, 53(7), 1708 (1970).

What is claimed is:
1. A compound of the formula:

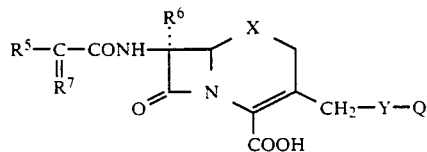

or a pharmaceutically acceptable salt or pharmaceutically acceptable ester thereof, wherein:
X is sulphur or sulphinyl;
$R^6$ is hydrogen, methoxy or formamido;
$R^5$ is 2-aminothiazol-4-yl or 2-aminooxazol-4-yl each unsubstituted or substituted in the 5-position by fluorine, chlorine or bromine, or $R^5$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;
$R^7$ is of the formula $=N.O.R^8$ (having the syn configuration about the double bond) wherein $R^8$ is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, carboxy(3-6C)alkenyl, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(1-4C)alkyl, (1-4C)haloalkylcarbamoyl(1-4C)alkyl, (1-3C)haloalkyl, (2-6C)hydroxyalkyl, (1-4C)alkoxy,(2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylaminol(1-6C)alkyl, (2-8C)dialkylamino(2-6C)alkyl, (1-5C)cyanoalkyl, 3-amino-3-carboxypropyl, 2-(amidinothio(ethyl, 2-(N-aminoamidinothio)ethyl, tetrahydropyran-2-yl, thietan-3-yl, 2-oxopyrrolidinyl, or 2-oxotetrahydrofuranyl, or $R^8$ is of the formula V:

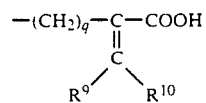

wherein q is one or two and $R^9$ and $R^{10}$ are independently hydrogen or $C_{1-4}$alkyl; or $R^8$ is of the formula VI:

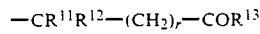

wherein r is 0-3, $R^{11}$ is hydrogen, (1-3C)alkyl or methylthio, $R^{12}$ is hydrogen, (1-3)alkyl, (3-7C)cycloalkyl, cyano, carboxy, (2-5C)carboxyalkyl or methanesulphonylamino, or $R^{11}$ and $R^{12}$ are joined to form, together with the carbon to which they are attached, a (3-7C)carbocyclic ring, and $R^{13}$ is hydroxy, amino, (1-4C)alkoxy, (1-4C)alkylamino or of the formula $NHOR^{14}$ in which $R^{14}$ is hydrogen or (1-4C)alkyl; or $R^7$ may be of the formula $=CH.R^{15}$ wherein $R^{15}$ is hydrogen, halogen, (1-6C)alkyl, (3-7C)cycloalkyl, (2-6C)alkenyl, (3-7C)cycloalkenyl, phenyl or benzyl;
Q is a group of the formula (III):

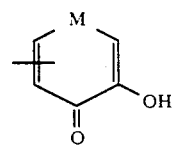

wherein M is oxygen or a group $NR^3$
wherein $R^3$ is hydrogen or $C_{1-4}$ alkyl;
ring Q is further unsubstituted or further substituted by $C_{1-4}$ alkyl, halo, hydroxy, hydroxy $C_{1-4}$ alkyl, cyano, trifluoromethyl, nitro, amino, $C_{1-4}$ alkylamino, di-$C_{1-4}$ alkylamino, amino $C_{1-4}$ alkyl, $C_{1-4}$ alkylamino $C_{1-4}$ alkyl, Di-$C_{1-4}$ alkylamino $C_{1-4}$ alkyl, $C_{1-4}$ alkanoyl, $C_{1-4}$ alkoxy, $C_{1-4}$ alkythio, $C_{1-4}$ alkanoyloxy, carbamoyl, $C_{1-4}$ alkylcarbamoyl, di-$C_{1-4}$ alkyl carbamoyl, carboxy, carboxy $C_{1-4}$ alkyl, sulpho, sulpho $C_{1-4}$ alkyl, $C_{1-4}$ alkanesulphonamido, $C_{1-4}$ alkoxycarbonyl, $C_{1-4}$ alkanoylamino, nitroso, thioureido, amidino, ammonium, mono-, di- or tri-$C_{1-4}$ alkylammonium or pyridinium;

Y, which links into the ring of formula (III) is:

or,

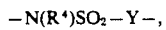

where $R^4$ is hydrogen, $C_{1-4}$ alkyl unsubstituted or substituted by any of halo, hydroxy, $C_{1-4}$ alkoxy, carboxy, amino, cyano, $C_{1-4}$ alkanoylamino, phenyl or heteroaryl, or $R^4$ is $C_{2-6}$ alkenyl; and $Y^1$ is a direct covalent bond, $C_{1-4}$ alkylene unsubstituted or substituted by any of $C_{1-4}$ alkyl, cyano, carboxy, $C_{1-4}$ alkoxycarbonyl, nitro, amino, $C_{1-4}$ alkylamino, di-$C_{1-4}$ alkylamino, $C_{1-4}$ alkanoylamino, $C_{1-4}$ alkoxy carbonylamino, hydroxy, halo, carbamoyl, $C_{1-4}$ alkylcarbomoyl, di-$C_{1-4}$ alkylcarbamoyl or trifluoromethyl, or $Y^1$ is carbonyl or $C_{2-4}$ alkenylene unsubstituted or substituted by $C_{1-4}$ alkyl.

2. The compound according to claim 1 wherein Q is a group of the formula (III) wherein M is —NH—.

3. The compound according to claim 1 wherein $R^4$ is hydrogen, methyl or ethyl.

4. The compound according to claim 1 wherein Y is —NHCO—, —NHSO$_2$— or N(C$_2$H$_5$)CO.

5. The compound according to claim 4 wherein Y is —NHCO—.

6. The compound according to claim 1 wherein X is sulphur.

7. The compound according to claim 1 wherein $R^6$ is hydrogen.

8. The compound according to claim 1 wherein $R^5$ is 2-aminothiazol-4-yl.

9. The compound according to claim 1 wherein $R^7$ is of the formula =NOR8 (having the syn configuration about the double bond) and R8 is 2-carboxyprop-2-yl.

10. The compound according to claim 1 which is:
7-[2-(2-aminothiazol-4-yl)-2-((Z)-1-carboxycyclopentoxyimino)acetamido]-3-(3,4-dihydroxypyridinylcarboxamidomethyl)ceph-3-em-4-carboxylic acid.

11. The compound according to claim 1 which is:
7-[2-(2-aminothiazol-4-yl)-2-((Z)-1-carboxy-1-methylethoxyimino)acetamido]-3-(3,4-dihydroxypyridinylcarboxamidomethyl)ceph-3-em-4-carboxylic acid.

12. The compound according to claim 1 which is:
7-[2-(2-aminothiazol-4-yl)-2-((Z)-1-carboxy-1-methylethoxyimino)acetamido]-3-(3-bromo-4,5-dihydroxypyridinylcarboxamidomethyl)ceph-3-em-4-carboxylic acid.

13. An antibacterial pharmaceutical composition which comprises an antibacterially effective amount of the compound according to claim 1 and a pharmaceutically acceptable carrier.

14. The composition according to claim 13 wherein Q of said compound is a group of the formula (III) wherein M is —NH—.

15. The composition according to claim 13 wherein $R^4$ of said compound is hydrogen, methyl or ethyl.

16. The composition according to claim 13 wherein Y of said compound is —NHCO—, —NHSO$_2$— or N(C$_2$H$_5$)CO.

17. The composition according to claim 13 wherein X of said compound is sulphur.

18. The composition according to claim 13 wherein $R^6$ of said compound is hydrogen.

19. The composition according to claim 13 wherein $R^5$ of said compound is 2-aminothiazol-4-yl.

20. The composition according to claim 13 wherein $R^7$ of said compound is of the formula =NOR8 (having the syn configuration about the double bond) and R8 is 2-carboxyprop-2-yl.

21. The composition according to claim 13 wherein said compound is:
7-[2-(2-aminothiazol-4-yl)-2-((Z)-1-carboxy-1-methylethoxyimino)acetamido]-3-(3,4,-dihydroxypyridinylcarboxamidomethyl)ceph-3-em-4-carboxylic acid.

22. A method of treating a bacterial infection in a mammal comprising administering to a mammal in need of such treatment an antibacterially effective amount of said compound according to claim 12.

23. The method according to claim 22 wherein Q of said compound is a group of the formula (III) wherein M is —NH—.

24. The method according to claim 22 wherein $R^4$ of said compound is hydrogen, methyl or ethyl.

25. The method according to claim 22 wherein Y of said compound is —NHCO—, —NHSO$_2$— or N(C$_2$H$_5$)CO.

26. The method according to claim 22 wherein X of said compound is sulphur.

27. The method according to claim 22 wherein $R^6$ of said compound is hydrogen.

28. The method according to claim 22 wherein $R^5$ of said compound is 2-aminothiazol-4-yl.

29. The method according to claim 22 wherein $R^7$ of said compound is of the formula =NOR8 (having the syn configuration about the double bond) and R8 is 2-carboxyprop-2-yl.

30. The method according to claim 22 wherein said compound is:
7-[2-(2-aminothiazol-4-yl)-2-((Z)-1-carboxy-1-methylethoxyimino)acetamido]-3-(3,4-dihydroxypyridinylcarboxamidomethyl)ceph-3-em-4-carboxylic acid.

* * * * *